(12) United States Patent
Weissbrodt et al.

(10) Patent No.: US 11,471,385 B2
(45) Date of Patent: Oct. 18, 2022

(54) CAPSULES WITH A HIGH ACTIVE INGREDIENT CONTENT

(71) Applicant: Symrise AG, Holzminden, NY (US)

(72) Inventors: Jenny Weissbrodt, Holzminden (DE); Frank Aickele, Holzminden (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 16/402,523

(22) Filed: May 3, 2019

(65) Prior Publication Data

US 2019/0321271 A1 Oct. 24, 2019

Related U.S. Application Data

(62) Division of application No. 15/303,940, filed as application No. PCT/EP2015/057918 on Apr. 11, 2015, now abandoned.

(30) Foreign Application Priority Data

Apr. 14, 2014 (EP) ..................................... 14164635

(51) Int. Cl.
| | |
|---|---|
| A61K 8/11 | (2006.01) |
| A61K 8/73 | (2006.01) |
| A61Q 19/00 | (2006.01) |
| A23L 27/00 | (2016.01) |
| A23L 33/10 | (2016.01) |
| A23G 4/08 | (2006.01) |
| A23L 2/52 | (2006.01) |

(52) U.S. Cl.
CPC .................. *A61K 8/11* (2013.01); *A23G 4/08* (2013.01); *A23L 2/52* (2013.01); *A23L 27/72* (2016.08); *A23L 33/10* (2016.08); *A61K 8/73* (2013.01); *A61K 8/733* (2013.01); *A61Q 19/00* (2013.01); *A61Q 19/007* (2013.01); *A23V 2002/00* (2013.01); *A61K 2800/41* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 8,119,175 B2 * | 2/2012 | Soper | ...................... A23L 27/12 426/98 |
| 2014/0335224 A1 | 11/2014 | Asche et al. | |
| 2018/0264076 A1 * | 9/2018 | Coulter | .................. A61K 47/44 |

FOREIGN PATENT DOCUMENTS

| | | |
|---|---|---|
| DE | 690 00 229 T2 | 3/1993 |
| DE | 691 04 576 T2 | 3/1995 |
| DE | 196 44 343 A1 | 4/1998 |
| DE | 100 26 453 A1 | 11/2001 |
| EP | 1 110 462 A2 | 6/2001 |
| EP | 1 295 538 A2 | 3/2003 |
| EP | 2801263 | 11/2014 |
| WO | 02/064246 A1 | 8/2002 |

OTHER PUBLICATIONS

Mandal et al. (Brazillian journal of Pharmaceutical Sciences vol. 46, n.4 (2010).

* cited by examiner

*Primary Examiner* — Patricia Duffy
*Assistant Examiner* — Garen Gotfredson
(74) *Attorney, Agent, or Firm* — Dilworth & Barrese, LLP

(57) ABSTRACT

The invention relates to (dried) capsules with a high active-ingredient or active-substance content, to the use of the capsules in cosmetic and/or pharmaceutical compositions and to the production of the capsules.

17 Claims, No Drawings

CAPSULES WITH A HIGH ACTIVE INGREDIENT CONTENT

CROSS REFERENCE TO RELATED APPLICATIONS

This application claims priority under 35 U.S.C. § 120 as a Division of pending Ser. No. 15/303,940, filed Oct. 13, 2016, the contents of which are incorporated herein by reference, in their entirety.

FIELD OF THE INVENTION

The invention concerns the field of (dried) capsules with a high active ingredient or active substance content, their use in cosmetic and/or pharmaceutical compositions, and the production of said capsules.

PRIOR ART

Encapsulations or enclosures of active ingredients, in particular flavoring agents or fragrances or cosmetic or pharmaceutically active ingredients, belong to prior art, and often provide the possibility of stabilizing the encapsulated or enclosed material and protecting it from reactions with the medium in order to obtain the effect of the active ingredient and slowly release it. There are various possibilities for encapsulation materials. A matrix material known to the person skilled in the art is alginate.

Alginates are linear polysaccharides whose monomeric building blocks are β-D-mannuronate and α-L-guluronate. The β-D-mannuronate and α-L-guluronate radicals in the alginate are linked to one another via 1,4-glycosidic bonds and form sequences with homopolymers and an alternating structure. The degree of polymerization is between 100 and 3000, which corresponds to a molar mass of 20,000 to 600,000 u. The homopolymer sequences are classified into two different categories: while the so-called "MM blocks" are composed of β-1,4-glycosidically linked D-mannuronate radicals, the "GG blocks" contain L-guluronate radicals having α-1,4-glycosidic bonds. In the third alginate block type, the sequence with the alternating structure and the D-mannuronate and L-guluronate radicals are alternately linked to one another via β-1,4 and α-1,4-glycosidic bonds. As a result, all four possible types of glycosidic bonds are present in the alginate: diequatorial (MM), diaxial (GG), equatorial-axial (MG), and axial-equatorial (GM).

Methods for the production of calcium alginate particles have also long belonged to prior art. The so-called drip feed method is often used in production. In this method, a solution of sodium alginate is added dropwise via a hollow needle or cannula to a solution of a crosslinking agent, e.g. a calcium salt solution (an "ionogenic crosslinker"). In order to prevent agglomeration, rotating or vibrating needles or cannulas can be used. Other divalent cations such as $Sr^{2+}$, $Ba^{2+}$, $Pb^{2+}$, $Cu^{2+}$, $Cd^{2+}$, $Co^{2+}$, $Ni^{2+}$, $Zn^{2+}$, and $Mn^{2+}$ are also suitable as ionogenic crosslinkers. However, their use is limited by their toxicity. The purely ionogenic crosslinking and the gelation of the alginate solution connected therewith chiefly result from replacement of the Na+ ions of the guluronate in the polymer by e.g. $Ca^{2+}$. The resulting special spatial arrangement of the guluronic acid sequences around the divalent $Ca^{2+}$ ion is known in the literature as the "egg box model" and is responsible for the structure of the resulting gel network. This imparts strength to the forming particles (beads). Spherical particles of alginate produced by dropwise addition of an alginate solution to a reservoir of an ionogenic crosslinker are widely known in the literature for encapsulation of a wide range of substances, e.g. yeast cells (T. Shiotani et. al., Eur. J. Appl. Microbial. Biotechnol. 13 (2), 1981), bacteria (H. Provost et. al., Biotechnology Letters, 7(4), 247-252, 1985), as well as therapeutic agents (U.S. Pat. No. 485,471). For incorporation purposes, the material to be encapsulated is added to the alginate solution prior to contact with the crosslinking medium.

DE 10026453 A1 discloses magnetic and non-magnetic spherical particles composed of a dimensionally stable alginate gel that is crosslinked by salt bridges between the carboxyl groups of the alginate. The spherical particles can contain incorporated magnetic material, alginate with a D-mannuronate (M): L-guluronate (G) ratio of 0.1:1 to less than 1:1, one or a plurality of cationic species, preferably a divalent or multivalent metal cation, and one or a plurality of agents with favorable properties.

The subject matter of EP 1110462 A2 (Nutrinova) is an encapsulated biologically active food ingredient composed of a core containing at least one dietary fiber which is surrounded by a biologically active substance and a capsule-forming substance surrounding the core, wherein the dietary fibers may be wheat fibers or pectin, the biologically active substance may be a nutrient, and the capsule-forming substance may be an emulsifier.

EP 1295538 A2 (Nutrinova) discloses dietary fiber capsules, the core of which contains locust bean fiber and is enclosed on all sides by capsule materials, with the capsule materials being selected from soluble dietary fibers, which may be alginate, pectin, gum arabic, or modified fibers.

EP 1508591 A1 (Symrise) discloses gelatin-free seamless capsules with a liquid core and a solid shell surrounding this core, with the shell being composed of agar, hydrolyzed starch, water, and one or more additives.

EP 2099889 B1 also discloses alginate capsules (beads), but for use in detergents, comprising.

EP 2340805 A2 (Blume) discloses nanocapsules containing at least the following components: a liquid lipid core and a continuous shell surrounding the core composed of at least one hydrophobically modified polysaccharide and at least one membrane-forming emulsifier.

EP 0766515 B1 concerns alginate capsules containing active ingredients which are released on a delayed basis. The alginate capsules have a composition in which the weight ratio of alginate to polyacrylic acid is 75:2 to 75:10 and the polyacrylic acid has a molecular weight of 10 to 250 kDa.

A problem with the particles of prior art, particularly when a high content of flavoring agents or fragrances is to be achieved, is that the capsules are microbially unstable in a wet state. Improved stability can be achieved by drying the capsules. In the drying process, however, the active ingredients encapsulated in the capsules, particularly when these are flavoring agents or fragrances, are frequently pressed out and unintentionally released, causing the particles to shrink and a portion of the encapsulated active ingredients (flavoring agents or fragrances) to be lost before actual use.

The object of the present invention was therefore to provide stable capsules containing active ingredients or substances which allow targeted release of the encapsulated active ingredients or substances, for example during heating, baking, or frying or on exposure to strong shearing forces such as chewing or rubbing. The object of the present invention was thus to develop capsules that are not water-based and are water-insoluble, as most foods and cosmetic products contain water, with the result that the required release on heating, consumption, or exposure to shearing forces is not achieved to an optimal extent or is achieved only in a very limited manner.

Another object of the present invention was to develop capsules that allow a variable content as well as a high content of active ingredients, so that the capsules can be used over the widest possible range of applications, such as in the cosmetic and pharmaceutical fields, particularly in the areas of oral care or dermatology. The active ingredients and substances in the capsules are to be water-insoluble in this case as well, and are only to be released by rubbing or shearing, e.g. on brushing the teeth or rubbing on the skin.

DESCRIPTION OF THE INVENTION

Capsules, comprising
(a) at least one gelable substance,
(b) at least one emulsifier,
(c) at least one filler, and
(d) at least one active ingredient an active substance of which is to be encapsulated, with the active ingredient (d) being dispersed in an emulsion comprising the gelable substance (a), the emulsifier (b), and the filler (c), are the subject matter of the invention.

In a preferred embodiment, the gelable substance a) is selected from the group composed of alginate, pectin, agar-agar, carrageenan, gellan gum, gelatins, modified cellulose, and/or proteins, the emulsifier b) is selected from the group composed of polysorbates, sugar esters, saponins, gum arabic, and/or modified starch, and the filler c) is selected from the group composed of vegetable fibers, microcrystalline cellulose, silica gels, native starch and/or silicates.

Surprisingly, it was found that when the capsule matrix is composed of an emulsion comprising at least one gelable substance, at least one emulsifier, and at least one filler, active ingredients or active substances can be incorporated into the capsule matrix in finely dispersed form. This results in a high active ingredient or active substance content of the capsule matrix with the desired active ingredient or active substance and increased stability of the capsules, so that the active ingredients or active substances are not pressed out in the capsule drying phase and unintentionally released or destroyed.

Preferably, the capsules according to the invention have an extremely high active ingredient content, which is variably adjusted according to application requirements. Accordingly, the capsules according to the invention preferably have an active ingredient content of 20 to 95 wt %. The active ingredient or active substance content depends on the final application of the capsules and therefore varies according to the field of use. For example, capsules containing flavoring agents or fragrances should preferably have a content of up to 95 wt %, while capsules used in the field of medicine should preferably have a content of therapeutically active ingredients of 20-60 wt %, and more preferably 30-50 wt %. In the field of medicine, the content of the capsules naturally also depends on the dosage and the desired amount of the active ingredient to be released. The capsules according to the invention can thus be loaded accordingly. The content can be correspondingly varied and adjusted depending on the application requirements. Accordingly, the aforementioned content ranges are to be understood as possible example values and by no means limit the producible content.

The use of the capsules according to the invention in toothpaste is particularly advantageous, as the capsules according to the invention have a particularly favorable stabilizing effect on the encapsulated substances in the toothpaste, allowing them to be released or delivered in a controlled manner at the time of use (brushing of the teeth). The encapsulated active ingredients or active substances are preferably cleaning agents, foaming agents, wetting and moisturizing agents, taste and flavoring agents, and preservatives, as well as dyes and additives, and in medicinal toothpastes or dental creams, active ingredients for prophylaxis, particularly of parodontitis and caries (fluoride). Preferably, such a capsule for use in toothpaste has a content of the active ingredients or active substances of 50 to 80 wt %, and in flavorings even up to 95 wt %.

The use of the capsules according to the invention in cosmetic products, in particular in the area of dermatology, such as (skin) creams, pastes, gels, and lotions, but also sprays, is also particularly advantageous, as the capsules according to the invention have the effect of particularly favorably stabilizing the desired substances, preferably fragrance and flavoring agents or cosmetic active substances, and only releasing them in a controlled manner at the time of use (by rubbing onto the skin). Preferably, in cosmetic products, such a capsule has a content of the active ingredients or active substances of 40 to 80 wt %, and in fragrances and flavorings, even as much as 95 wt %.

Preferably, the capsules according to the invention can have an average diameter of 200 to 1500 µm, preferably 400 to 900 µm, and particularly preferably 500 to 800 µm. The capsule size can be varied and adjusted accordingly depending on the application requirements. Accordingly, the aforementioned capsule size ranges are to be understood as possible example values and by no means limit the producible capsule sizes.

In the present application, the term capsule is used as a synonym for the term particle. The two terms are to be understood as being equivalent and mutually interchangeable.

In the present application, "gelable substances" are understood to be compounds which swell (up) in water or bind water, thus causing gelation and forming a gelatinous mass.

Suitable gelable substances that can be used according to the invention are selected from the group composed of alginate, pectin, agar-agar, carrageenan, gellan gum, gelatins, modified cellulose, and/or proteins.

Particularly preferred are alginate, pectin, carrageenan and/or gellan gum, and most particularly preferred are alginate and/or pectin and/or gellan gum, so that in a preferred embodiment, the gelable substance is alginate and/or pectin and/or gellan gum, and so that the resulting capsules are alginate based and/or pectin based and/or gellan gum based capsules, preferably pectin or alginate or alginate-pectin or alginate-gellan gum based capsules.

Preferably, in a mixture of alginate and pectin or alginate and gellan gum, the capsules according to the invention show a preferred ratio of alginate to pectin of 1:2 to 2:1, and preferably a ratio of alginate to gellan gum of 3:2 to 3:1.

Alginate is the general designation for alginic acid and its salts. The M:G ratio of the alginate used in the present application is preferably 0.1:1 to less than 1:1, for example 0.1:1 to 0.99:1. This means that in the alginate used, the number of G radicals is greater than that of the M radicals. The M:G ratio is preferably 0.1:1 to 0.8:1, and particularly preferably 0.2:1 to 0.8:1. Suitable algae genera for the production of alginate include *Laminaria, Ecklonia, Macrocystis, Lessonia, Ascophyllum*, and *Durvillea*.

Sodium alginate (E 401), potassium alginate (E 402), ammonium alginate (E 403), calcium alginate (E 404), or propylene glycol alginate (PGA, E 405) is preferably used as the alginate. Suitable alginates are available under the brand name "Manguel" (Manguel GMB) from the firm International Speciality Products, under the brand name "Protonal" from the firm FMC BioPolymer, and under the brand names "Satialgine", "Cecalgum" and "Algogel" from the firm Texturant Systems.

The cationic species for forming a gel matrix with the alginate can basically be any species that is capable of forming a gel matrix with the alginate. Metal cations are preferred, particularly those which form divalent or polyvalent metal salts in an aqueous solution.

According to the invention, therefore, in the case of an aqueous solution of an alkali or ammonium salt of alginic acids or pectic acids, crosslinking agents are used that preferably contain a divalent cation, preferably calcium. According to the invention, when carrageenan is used, a crosslinking agent, preferably with potassium ions, is used.

Pectins are vegetable polysaccharides, more specifically polyuronides. The substance class of the pectins occurs in numerous structures. All of these structures have in common that they are polysaccharides whose main component (to at least 65 wt %) is α-D-galacturonic acid (pKa value 2.9) as a monomer. These galacturonic acid monomers are bonded to one another via α-1,4-, and usually also to a minor extent via β-1,4-glycosidic bonds, and thus form the backbone of the pectin molecule. This linear backbone is periodically interrupted by 1,2-bonds with α-L-rhamnose. The systematic name for pectin is therefore rhamnogalacturonic acid.

The incorporation of rhamnose units leads to disturbances in the formally linear polygalacturonic acid chain: the chains are "kinked". On the other hand, the rhamnose structural elements in natural pectins bear oligomeric side chains composed of the sugars arabinose, galactose or xylose. In turn, these neutral sugar side chains can be classified into arabinans, galactans, and arabinogalactan I, as well as arabinogalactan II, which is bonded to proteins, but is often also included among the hemicelluloses. The side chains usually consist of 1 to 50 sugar units. In industrial production of pectins, these side chains are largely lost, in particular the acid-labile arabinofuranose. The branched regions of the chain caused by L-rhamnose and its side chains do not occur regularly, but accumulate in the so-called "hairy regions". In contrast, the linear parts of the chain are referred to as "smooth regions".

In addition to this branching of the main chain, the pectin macromolecule also has other characteristics. The hydroxy groups on the $C_2$ or $C_3$ atom of the galacturonic acid units are acetylated or substituted to a minor extent by further neutral sugars such as D-galactose, D-xylose, L-arabinose, or L-rhamnose-predominantly in the hairy regions in this case as well. The carboxy groups of the polygalacturonic acid are often esterified with methanol. The degree of esterification and acetylation fluctuates depending on the origin of the pectin, but is of decisive importance for the chemical properties. Pectins are therefore classified based on their average degree of esterification VE.

Pectins are found in all higher land plants. In this case, pectins are found in all of the more solid components, such as the stems, flowers, leaves, etc. Particularly rich in pectin are plant parts having relatively tough/hard components, e.g. citrus fruits or inflorescences of sunflowers. The pectin content varies from plant to plant; for example, apples contain approx. 1-1.5%, oranges approx. 0.9-3.5%, citrus peels (from oranges and lemons) approx. 30%, apricots approx. 1%, cherries approx. 0.4%, carrots approx. 1.4%, oranges approx. 0.5-3.5%, and quinces approx. 0.5% pectin.

Suitable pectins for the present invention are apple, citrus, and grapefruit pectins, which are available for example from the firm Herbstreith & Fox.

Suitable gelable substances that are modified cellulose are preferably selected from methyl cellulose (MC), hydroxyethyl cellulose (HEC) and carboxymethyl cellulose (CMC), hydroxypropyl methylcellulose (HPMC), and hydroxypropyl cellulose (HPC) and ethyl hydroxyethyl cellulose (EHEC).

Suitable gelable substances that are starch (derivatives) are preferably selected from e.g. hydroxyethyl starch and hydroxypropyl starch.

The gelable substance, which is preferably alginate and/or pectin and/or gellan gum, is preferably used in an amount of 0.5 to 3 wt % with reference to the total weight of a capsule. Preferably, the gelable substance is used in an amount of 0.7 to 2.0 wt %, particularly preferably in an amount of 1.0 to 1.7 wt %, and most preferably in an amount of 1.1 to 1.5 wt % on a dry matter basis with respect to the total weight of a capsule.

Suitable emulsifiers according to the invention are selected from the group composed of polysorbates, sugar esters, saponins, gum arabic, modified gum arabic, and/or modified starch.

Preferably, the following polysorbates are used:
polysorbate 20 (polyoxyethylene (20) sorbitan monolaurate) (E 432)
polysorbate 21 (polyoxyethylene (4) sorbitan monolaurate)
polysorbate 40 (polyoxyethylene (20) sorbitan monopalmitate) (E 434)
polysorbate 60 (polyoxyethylene (20) sorbitan monostearate) (E 435)
polysorbate 61 (polyoxyethylene (4) sorbitan monostearate)
polysorbate 65 (polyoxyethylene (20) sorbitan tristearate) (E 436)
polysorbate 80 (polyoxyethylene (20) sorbitan monooleate) (E 433)
polysorbate 81 (polyoxyethylene (5) sorbitan monooleate)
polysorbate 85 (polyoxyethylene (20) sorbitan trioleate) (Span 85)
polysorbate 120 (polyoxyethylene (20) sorbitan monoisostearate).

In a preferred embodiment, the emulsifiers are selected from the group composed of gum arabic, modified gum arabic, and/or modified starch.

Suitable fillers according to the invention are selected from the group composed of vegetable fibers, microcrystalline cellulose, silica gels, native starch, and/or silicates. Fiber plants are preferably used as fillers.

Accordingly, in a preferred embodiment of the invention, the filler used is a vegetable fiber selected from apple fibers, bamboo fibers, oat fibers, pea fibers, potato fibers, and/or wheat fibers. Suitable fibers are available for example from the firm JELUCEL under the brand names JELUCEL® WF, JELUCEL® BF, JELUCEL@ OF, or also in the Vitacel® product line of the firm JRS. Particularly preferred in this case are apple fibers, bamboo fibers, oat fibers, and/or wheat fibers.

The filler is preferably used in an amount of 0.5 to 5 wt % relative to the total weight of the capsule. More preferably, the filler is used in an amount of 0.7 to 3.5 wt %, and even more preferably in an amount of 0.8 to 1.5 wt % relative to the total weight of a capsule.

A particular challenge of the present invention was drying of the high-content capsules. It was important to produce capsules in which the active ingredient, which is enclosed in matrix, is not pressed out by drying, causing it to be released or destroyed prior to use.

A particular advantage of the capsules according to the invention is that they can be easily dried without causing a major loss of the enclosed active ingredients and active substances (due to uncontrolled release). Therefore, the capsules according to the invention should preferably have an AW value of less than or equal to 0.8, preferably less than or equal to 0.7, and particularly preferably less than or equal to 0.6. The AW value is the measure of unbound and loosely bound water, i.e. of the availability of water in food products or foodstuffs and preparations. [1]The AW value is therefore an important parameter for the shelf life of foods. The higher the AW value, i.e. the more unbound water a food contains, the more readily it can spoil. The reason is that the freely available water is of decisive importance mainly for the growth or metabolism of microorganisms. It is also required by some enzymes, the so-called hydrolases, for hydrolysis, i.e. for the cleavage of chemical bonds by a reaction with water.

[1] http://www.lebensmittellexikon.de/a0000420.php

For successful drying of the capsules, the combination according to the invention of emulsifiers, preferably emulsifiers suitable for foodstuffs, and fillers is of decisive importance.

A ratio of the emulsifier to the filler is preferably in the range of 2.1:1.2, and particularly preferably in the range of 1:1.

The use of the aforementioned fillers has the particular advantage of increasing the dry matter in the capsule and binding the active ingredient or the active substance encapsulated in the matrix, providing stability during drying. For this reason, the filler is an essential component of the present invention.

Depending on the requirements of the final application, the capsule properties can be controlled by the selection and amount of the emulsifier and the filler, thus affecting properties such as the release behavior of the active ingredient and the stability of the capsule and its contents.

A further advantage of the capsules according to the invention is their stability, which makes it possible to use said capsules in a wide variety of different applications, in order to bring the desired active ingredients and active substances according to the application requirements into the corresponding medium and release them in a controlled manner as needed.

Accordingly, a further preferred embodiment of the present invention comprises capsules containing active ingredients or active substances selected from the group composed of flavorings, fragrances, dietary supplements such as vitamins, minerals, antioxidants, anthocyanins, coenzyme 10, etc., as well as cosmetic active substances and/or pharmaceutically active substances.

Moreover, a preferred embodiment of the invention is use of the capsules according to the invention in cosmetic products, pharmaceutical agents, or foods and beverages.

Further subject matter of the invention is the production of the capsules according to the invention. The method for production of the capsules according to the invention comprises (i) formation of a mixture of
 (a) at least one gelable substance,
 (b) at least one emulsifier,
 (c) at least one filler, and
 (d) at least one active ingredient or an active substance, (ii) addition of drops of the mixture of i) to a solution of a multivalent cation, so that crosslinking occurs and gelation takes place, (iii) separation of the capsules formed from step ii), and (iv) drying of the capsules obtained from step iii).

The subject matter of the invention further includes capsules which can be obtained by means of the steps, comprising:

(i) formation of a mixture of a) at least one gelable substance, b) at least one emulsifier, c) at least one filler, and d) at least one active ingredient or active substance, (ii) addition of drops of the mixture of i) to a solution of a multivalent cation, so that crosslinking occurs and gelation takes place, (iii) separation of the capsules formed from step ii), and (iv) drying of the capsules obtained from step iv), wherein the gelable substance a) is selected from the group composed of alginate, pectin, agar-agar, carrageenan, gellan gum, gelatins, modified cellulose, and/or proteins, the emulsifier b) is selected from the group composed of polysorbates, sugar esters, saponins, gum arabic, and/or modified starch, and c) the filler is selected from the group composed of vegetable fibers, microcrystalline cellulose, silica gels, native starch, and/or silicates.

According to the invention, an emulsion of a) at least one gelable substance, b) at least one emulsifier, c) at least one filler, and d) at least one active ingredient or an active substance is produced. Discrete droplets are than produced from the emulsion, and these are placed in a cell bath of multivalent cations, with the result that dimensionally stable, essentially water-insoluble capsules are produced. Advantageously, an alcohol-based solution, which preferably contains calcium ions, should be used.

In producing the droplets, the particle size can be adjusted by means of the dimensions of the needles/cannulas used. The use of rotating or vibrating needles/cannulas is also advantageous, as this allows more favorable shearing off of the droplets. The use of a mobile precipitation bath is also advantageous, so that the drops formed can be transported further and cannot agglomerate in one place.

The capsules obtainable in this manner can be rinsed with water to remove salt residues.

Drying of the capsules is carried out by fluidized bed drying, in which the capsules to be dried are preferably placed in a stream of warm air coming from below and thus suspended, mixed, and dried.

Preferably, the wet material is turbulently mixed in a hot stream of gas directed upward and can thus dry with high heat and material transfer coefficients. The required gas flow rate preferably depends essentially on the particle size and density. The use of a perforated floor (hole sheet, Conidur sheet, floors of fabric or sintered material) can preferably prevent the solid material from falling through into the hot gas chamber. Heat is preferably supplied either by the drying gas or additional heat exchangers (tube bundles or plates) can preferably be added to the fluidized bed.

The fluidized bed dryers used for drying can be operated either continuously or batch-wise. In continuous operation, the residence time in the dryer is preferably several minutes to hours; the unit is therefore also suitable for long-term drying. If a narrow residence time distribution is required, a cascade fluidized bed can be used, preferably by means of separator plates, or the product flow can be made to approximate a perfect piston flow using meandering installations. In particular, larger dryers are preferably subdivided into several drying zones, which are operated with different gas flow rates and temperatures. The last zone can then be used as a cooling zone. In the feeding area of the wet material, particular care should be taken to ensure that no clumping occurs. There are various possible ways of accomplishing this, e.g. using a locally higher gas flow rate or an agitator.

In such a method, alginate and/or pectin and/or gellan gum based capsules are preferably produced. The capsules according to the invention are preferably water insoluble and stable. The wall material of the capsules according to the invention is composed of a matrix of water-insoluble, multivalent cations, preferably calcium ions, and a filler, and the active ingredients or active substances are preferably embedded in the matrix. The capsules according to the invention preferably do not show a typical core-shell structure in which the active ingredient or the active substance is enclosed in core and surrounded by a shell. Rather, the active ingredients or active substances should be embedded in the capsule matrix is a dispersed manner.

In a preferred embodiment, the capsules according to the invention are particularly suitable for use in cosmetic products, pharmaceutical agents, or foods and beverages.

Moreover, further subject matter of the present invention is the use of the capsules according to the invention for the production of cosmetic products, pharmaceutical agents, or foods and beverages.

Moreover, further subject matter of the present invention is the use of the capsules according to the invention for the production of pharmaceutical agents or cosmetic products for use on the skin or oral use.

In particular, the capsules according to the invention are suitable for enclosing the active ingredient and active substances in the matrix so that these can later be released in a controlled manner. Accordingly, in a preferred embodiment, the capsules according to the invention are used for the controlled, prolonged, and delayed delivery or release of active ingredients and active substances.

Preferably, the capsules according to the invention are used for the production of pharmaceutical agents or cosmetic products, which are particularly suitable for use on the skin. Preferred in this case are both cosmetic products and pharmaceutical agents in the form of ointments, creams, lotions, gels and pastes, and sprays.

Preferably, an ointment, cream, lotion, gel, and paste is understood to be a semisolid spreadable preparation which is suitable for application to the skin.

Such preparations, for example, may be based on an aqueous (hydrophilic) and an oily or fatty (lipophilic) component, with one component being distributed in the other in the form of an emulsion.

Hydrophilic creams of the O/W type or lipophilic creams of the W/O type may also be used. There are also creams that cannot be clearly classified as either the O/W or the W/O type which consist of gel-like lipophilic and hydrophilic phases that are coherently distributed in one another (amphiphilic cream). Multiple emulsion structures of the W/O/W emulsion type are also possible. In this case, however, the inner phase is in the form of an emulsion. Tiny water droplets are also embedded in the inner oil phase. This emulsion type is intended to combine the advantages of both W/O and O/W emulsions.

Further preparations are preferably ointments, as a rule in the form of a semisolid and homogenous appearing preparation that is suitable for use on the skin (e.g. as a wound ointment) or the mucous membranes. Ointments are usually used for local application of the active ingredient or for the care and protection of the skin or mucous membranes. Preferably, an ointment is composed of a hydrophobic or hydrophilic base of natural or synthetic substances and can be a single-phase (e.g. Vaseline) or multi-phase (e.g. water-in-oil) system.

A further preferred preparation is the gel. Gels can be described as viscoelastic fluids. Their fluid properties thus lie between those of an ideal liquid and those of an ideal solid. A gel is a finely-dispersed system of at least one solid and one liquid phase. The solid phase forms a sponge-like three-dimensional network whose pores are filled with a liquid (lyogel) or a gas (xerogel). If the network is highly porous and the incorporated gas is air, the gel is referred to as an aerogel. In this case, the two phases interfuse completely (bicoherence).

Preferably, preparations are also in the form of pastes. A paste is solid-liquid mixture (suspension) with a high content of solids. Pastes are preferably no longer flowable, but can be spread. For example, a paste is an ointment-powder mixture, and in particular a semisolid dosage form with a high content of dispersed solids (a "suspension ointment" with a solid content of 30 wt %-example of such a paste is Pasta Zinci (zinc ointment)).

An example in which a product may be in a variety of preparation forms is that of toothpaste (or dental cream or gel), which can be used in both the medical and cosmetic fields, and thus constitutes a broad product range. The main components are cleaning agents, foaming agents, wetting and moisturizing agents, taste and flavoring agents, and preservatives, as well as dyes and additives. Moreover, toothpastes also contain active ingredients for dental prophylaxis, particularly of parodontitis and caries (fluoride).

The capsules according to the invention allow active ingredients and active ingredient substances to be incorporated in a particularly favorable manner into the above-described preparations (ointments, creams, lotions, gels and pastes), as the capsules are water-insoluble and therefore stable in the base preparation, and are not destroyed, allowing the active ingredients or active substances to be released or delivered only at the time of use, preferably by mechanical shearing forces such as rubbing onto the skin or brushing of the teeth.

The capsules according to the invention are suitable in particular for use or incorporation in the aqueous/water-based medium, as the capsules are softened and caused to swell slightly by the surrounding water. This phenomenon allows the capsules, during use in particular in ointments, creams, lotions, gels and pastes, to show very favorable properties in rubbing and spreading onto the skin, thus making it possible to release the active ingredients and active substances in a controlled manner.

It is also possible to use the capsules according to the invention in foods and beverages. Here, the focus is on special foods and beverages for which specified substances are to be encapsulated and then later released at the time of use.

The foods and beverages are preferably spreadable food products such as bread spreads, meat paste, but also baked goods such as bread, dry biscuits, cakes, waffles and other pastries, sweets (such as chocolates, chocolate bar products, other products in bar form, fruit gums, hard and soft caramels, chewing gum), snack articles (such as baked or fried potato chips or potato dough products, maize or peanut-based extrudates), fat- and oil-based products or emulsions thereof (such as margarine, mayonnaise, remoulade, dressings), milk products (such as yoghurt, creams, spreads), and delicatessen products such as chicken salads.

Particularly preferred here are snacks, baked goods, margarine, spreads, and sweets such as chewing gums and fruit gums.

Preferably, in use in foods and beverages, flavoring agents are encapsulated in the capsules according to the invention in order to achieve a so-called "flavor burst effect" on consumption. For example, fruit flavoring agents such as orange, strawberry, apple flavors, etc. can be encapsulated in the capsules according to the invention, and these capsules can then for example be incorporated into chicken salad, chocolate, or ice cream, producing a surprising effect when these foods are chewed. A particular taste experience is also provided if, for example, the flavor-containing capsules according to the invention are baked into frozen waffles, cookies, or the like, so that a surprising flavor effect can be achieved on consumption.

Chewing Gums

The preferred oral preparations can also be chewing gums. These products typically comprise a water-insoluble and a water-soluble component.

The water-insoluble base, which is also referred to as the "gum base", ordinarily comprises natural or synthetic elastomers, resins, fats and oils, plasticizers, fillers, dyes and optionally waxes. The amount of base in the total composition is ordinarily 5 to 95, preferably 10 to 50, and in particular 20 to 35 wt %. In a typical embodiment of the invention, the base is composed of 20 to 60 wt % synthetic elastomers, 0 to 30 wt % natural elastomers, 5 to 55 wt % plasticizers, 4 to 35 wt % fillers and, in subordinate amounts, additives such as dyes, antioxidants and the like, with the proviso that they are water-soluble at most in small amounts.

Suitable synthetic elastomers are, for example, polyisobutylenes having average molecular weights (according to GPC) of 10,000 to 100,000 and preferably 50,000 to 80,000, isobutylene-isoprene copolymers ("butyl elastomers"), styrene-butadiene copolymers (styrene:butadiene ratio e.g. from 1:3 to 3:1), polyvinyl acetates having average molecular weights (according to GPC) of 2000 to 90,000 and preferably 10,000 to 65,000, polyisoprenes, polyethylene, vinyl acetate-vinyl laurate copolymers, and mixtures thereof. Examples of suitable natural elastomers are rubbers such as smoked or liquid latex or guayule, as well as natural rubbers such as jelutong, lechi caspi, perillo, sorva, massaranduba balata, massaranduba chocolate, nispero, rosindinba, chicle, gutta hang kang, and mixtures thereof. The choice of synthetic and natural elastomers and the mixing ratios thereof is essentially determined by whether bubbles are to be produced with the chewing gums (bubble gums) or not. Elastomer mixtures comprising jelutong, chicle, sorva, and massaranduba are preferably used.

In most cases, the elastomers are found to be too hard or to have insufficient deformability in processing, so that it has been found to be advantageous to use special plasticizers together with them, which of course must also meet in particular all the requirements for approval as food additives. In this respect, primarily suitable compounds are esters of resin acids, for example esters of lower aliphatic alcohols or polyols with wholly or partially hardened, monomeric or oligomeric resin acids. In particular, methyl, glycerol, or pentaerythritol esters and mixtures thereof are used for this purpose. Alternatively, terpene resins, which can be derived from α-pinene, α-pinene, 6-limonene, or mixtures thereof, can also be used.

Suitable examples of fillers or texturizing agents include magnesium or calcium carbonate, ground pumice, silicates, particularly magnesium or aluminum silicates, clays, aluminum oxides, talcum, titanium dioxide, and mono-, di-, and tricalcium phosphate, as well as cellulose polymers.

Suitable emulsifiers are tallow, hardened tallow, hardened or partially hardened vegetable oils, cocoa butter, partial glycerides, lecithin, triacetin, and saturated or unsaturated fatty acids with 6 to 22 and preferably 12 to 18 carbon atoms, and mixtures thereof.

Examples of suitable dyes and whitening agents include the FD and C types approved for the coloring of foods, plant and fruit extracts, as well as titanium dioxide.

The basic materials can contain waxes or be wax-free; examples of wax-free compositions can be found inter alia in patent specification U.S. Pat. No. 5,286,500, the contents of which are hereby expressly incorporated by reference.

In addition to the water-insoluble gum base, chewing gum preparations regularly contain a water-soluble component, composed for example of softeners, sweeteners, fillers, flavorings, flavor enhancers, emulsifiers, dyes, acidifiers, antioxidants, and the like, provided in this case that the components have at least sufficient water solubility. Depending on the water solubility of the special components, therefore, the individual components can belong both to the water-insoluble and the water-soluble phase. However, it is also possible to use combinations, for example of a water-soluble and a water-insoluble emulsifier, with the individual components being in different phases. Ordinarily, the water-insoluble component accounts for 5 to 95%, and preferably 20 to 80 wt % of the preparation.

Water-soluble softeners or plasticizers are added to the chewing gum compositions in order to improve chewability and chewing feel, and are typically contained in the mixtures in amounts of 0.5 to 15 wt. Typical examples are glycerol, lecithin, aqueous solutions of sorbitol, hydrogenated starch hydrolysates, and corn syrup.

Both sugar-containing and sugar-free compounds are suitable as sweeteners and are used in amounts of 5 to 95, preferably 20 to 80, and in particular 30 to 60 wt-relative to the chewing gum composition. Typical saccharide sweeteners are sucrose, dextrose, maltose, dextrin, dried invert sugar, fructose, levulose, galactose, corn syrup, and mixtures thereof. Suitable sugar substitutes include sorbitol, mannitol, xylitol, hydrogenated starch hydrolysate, maltitol and mixtures thereof. Other suitable additives include so-called HIAS (high intensity artificial sweeteners) such as sucralose, Aspartame, acesulfame salts, Alitame, saccharin and saccharin salts, cyclamic acid and salts thereof, glycyrrhizin, dihydrochalcone, thaumatin, monellin and the like, individually or in mixtures. Particularly effective compounds also include the hydrophobic HIAS, the subject matter of International Patent Application WO 2002 091849 A1 (Wrigley's) as well as Stevia extracts and their active components, in particular ribeaudioside A. The amount of these substances used depends chiefly on their performance capacity and is typically in the range of 0.02 to 8 wt %.

Suitable fillers for the production of low-calorie chewing gums in particular include polydextrose, Raftilose, Rafitiline, fructooligosaccharides (NutraFlora), palatinose oligosaccharides, guar gum hydrolysates (Sun Fiber), and dextrins.

The choice of further flavorings is virtually unlimited and is not of critical importance for the nature of the invention. The total amount of all flavorings is ordinarily 0.1 to 15 wt % and preferably 0.2 to 5 wt % relative to the chewing gum composition. Suitable further flavorings are, for example, essential oils, synthetic flavors and the like, such as aniseed oil, star anise oil, cumin oil, eucalyptus oil, fennel oil, lemon oil, wintergreen oil, clove oil and the like, as are also used, for example, in oral and dental care compositions.

The chewing gums can further comprise further auxiliary substances and additives which are suitable, for example, for tooth care, especially for controlling plaque and gingivitis, such as chlorhexidine, CPC, or triclosan. pH regulators (e.g. buffers or urea), active ingredients against caries (e.g. phosphates or fluorides), and biogenic active ingredients (antibodies, enzymes, caffeine, plant extracts) can further be present, provided that these substances are approved for foodstuffs and do not interact with one another in an undesirable manner.

Cosmetic and/or Pharmaceutical Agents

The capsules according to the invention are particularly suitable for incorporating active ingredients and substances into cosmetic products and/or pharmaceutical agents.

Preferably, therapeutically active ingredients can be encapsulated in the capsules according to the invention. Cosmetic products and pharmaceutical agents preferably comprise a number of auxiliary substances and additives. As needed, these auxiliary substances and additives can also be encapsulated in the capsules according to the invention. Examples of typical auxiliary substances and additives that can be contained in cosmetic products and/or pharmaceutical agents and can also be encapsulated in the capsules according to the invention include mild surfactants, oil components, emulsifiers, pearlescent waxes, cooling agents, bodying agents, thickeners, superfatting agents, stabilizers, polymers, silicone compounds, fats, waxes, lecithins, phospholipids, UV protection factors, humectants, biogenic active ingredients, antioxidants, deodorants, antiperspirants, antidandruff agents, film-forming agents, swelling agents, insect repellents, self-tanning agents, tyrosine inhibitors (depigmenting agents), hydrotropes, solubilizers, preservatives, perfume oils, dyes and the like.

In particular, active ingredients such a cooling active ingredients are suitable for being encapsulated in the capsules according to the invention. In such encapsulation, it is preferable to carry out cooling, e.g. in creams, pastes, sprays etc. only at the time of use, i.e. on rubbing onto the skin. The capsules according to the invention are particularly suitable for such use, e.g. as after-sun cream or after-sun sprays.

Surfactants

As surface-active substances, anionic, nonionic, cationic and/or amphoteric or zwitterionic surfactants whose content of the agents is ordinarily approximately 1 to 70, preferably 5 to 50, and in particular 10 to 30 wt % may be included. Typical examples of anionic surfactants are soaps, alkyl benzene sulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and the salts thereof, fatty acid isethionates, fatty acid sarcosinates, fatty acid taurides, N-acylamino acids such as acyl lactylates, acyl tartrates, acyl glutamates, and acyl aspartates, alkyl oligoglucoside sulfates, protein fatty acid condensation products (in particular wheat-based plant products) and alkyl (ether) phosphates. If the anionic surfactants contain polyglycol ether chains, these may exhibit a conventional, but preferably a narrowed homolog distribution. Typical examples of nonionic surfactants are fatty alcohol polyglycol ethers, alkyl phenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucuronic acid derivatives, fatty acid N-alkyl glucamides, protein hydrolysates (in particular wheat-based plant products), polyol fatty acid esters, sugar esters, sorbitan esters, polysorbates and amine oxides. If the nonionic surfactants contain polyglycol ether chains, these may exhibit a conventional, but preferably a narrowed homolog distribution. Typical examples of cationic surfactants are quaternary ammonium compounds such as dimethyl distearylammonium chloride, and esterquats, in particular quaternized fatty acid trialkanolamine ester salts. Typical examples of amphoteric or zwitterionic surfactants are alkyl betaines, alkylamidobetaines, aminopropionates, aminoglycinates, imidazolinium betaines and sulfobetaines. The above-mentioned surfactants are exclusively known compounds. Typical examples of particularly suitable mild surfactants, i.e. particularly gentle to the skin, are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkyl amidobetaines, amphoacetals and/or protein fatty acid condensates, the latter preferably based on wheat proteins.

Oil Components

Examples of suitable oil components include Guerbet alcohols based on fatty alcohols with 6 to 18, and preferably 8 to 10 carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$ fatty acids with branched alcohols, in particular 2-ethyl hexanol, esters of $C_{16}$-$C_{38}$ alkyl hydroxycarboxylic acids with linear or branched $C_6$-$C_{22}$ fatty alcohols, in particular dioctyl malate, esters of linear and/or branched fatty acids with multivalent alcohols (such as propylene glycol, dimer diol or trimer triol) and/or Guerbet alcohols, triglycerides based on $C_6$-$C_{10}$ fatty acids, liquid mono/di/triglyceride mixtures based on $C_6$-$C_{10}$ fatty acids, esters of $C_6$-$C_{22}$ fatty alcohols and/or Guerbet alcohols with aromatic carboxylic acids, in particular benzoic acid, esters of $C_6$-$C_{12}$ dicarboxylic acids with linear or branched alcohols with 1 to 22 carbon atoms or polyols with 2 to 10 carbon atoms and 2 to 6 hydroxyl groups, vegetable oils, branched primary alcohols, substituted cyclohexanes, linear and branched $C_6$-$C_{22}$ fatty alcohol carbonates such as dicaprylyl carbonate (Cetiol@ CC), Guerbet carbonates based on fatty alcohols with 6 to 18, and preferably 8 to 10 carbon atoms, esters of benzoic acid with linear and/or branched $C_6$-$C_{22}$ alcohols (e.g. Finsolv® TN), linear or branched, symmetrical or asymmetrical dialkyl ethers with 6 to 22 carbon atoms per alkyl group such as dicaprylyl ether (Cetiol®, OE), ring-opening products of epoxidized fatty acid esters with polyols, silicone oils (cyclomethicones, silicone methicone types, etc.) and/or aliphatic or naphthenic hydrocarbons such as squalane, squalene, or dialkyl cyclohexane.

Emulsifiers

Emulsifiers which may be used are for example nonionogenic surfactants from at least one of the following groups:

- addition products of 2 to 30 mol of ethylene oxide and/or 0 to 5 mol of propylene oxide onto linear fatty alcohols with 8 to 22 carbon atoms, fatty acids with 12 to 22 carbon atoms, alkyl phenols with 8 to 15 carbon atoms in the alkyl group, as well as alkylamine with 8 to 22 carbon atoms in the alkyl radical;
- alkyl and/or alkenyl oligoglycosides with 8 to 22 carbon atoms in the alk(en)yl radical and ethoxylated analogs thereof;
- addition products of 1 to 15 mol of ethylene oxide onto castor oil and/or hardened castor oil;
- addition products of 15 to 60 mol of ethylene oxide onto castor oil and/or hardened castor oil;
- partial esters of glycerol and/or sorbitan with unsaturated, linear or saturated, branched fatty acids with 12 to 22 carbon atoms and/or hydroxycarboxylic acids with 3 to 18 carbon atoms as well as adducts thereof with 1 to 30 mol of ethylene oxide;
- partial esters of polyglycerol (average intrinsic degree of condensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids with 12 to 22 carbon atoms and/or hydroxycarboxylic acids with 3 to 18 carbon atoms, as well as adducts thereof with 1 to 30 mol of ethylene oxide;
- mixed esters of pentaerythritol, fatty acids, citric acid and fatty alcohol and/or mixed esters of fatty acids with 6 to 22 carbon atoms, methyl glucose and polyols, preferably glycerol or polyglycerol;
- mono-, di- and trialkyl phosphates as well as mono-, di- and/or tri-PEG alkyl phosphates and salts thereof;
- wool wax alcohols;
- polysiloxane/polyalkyl/polyether copolymers or corresponding derivatives;
- block copolymers, e.g. polyethylene glycol-30 dipolyhydroxystearate;
- polymer emulsifiers, e.g. Pemulen grades (TR-1,TR-2) from Goodrich or Cosmedia® SP from Cognis;
- polyalkylene glycols, and
- glycerol carbonate.

In the following, particularly suitable emulsifiers are discussed in further detail:

Alkoxylates.

The addition products of ethylene oxide and/or propylene oxide onto fatty alcohols, fatty acids, alkyl phenols or castor oil are known, commercially available products. These are homologous mixtures whose average degree of alkoxylation corresponds to the ratio of the amounts ethylene oxide and/or propylene oxide and substrates with which the addition reaction is carried out. $C_{12/18}$ a fatty acid mono- and diesters of addition products of ethylene oxide to glycerol are known as refatting agents for cosmetic preparations.

Alkyl and/or Alkenyl Oligoglycosides.

Alkyl and/or alkenyl oligoglycosides, their production, and their use are known from prior art. They are produced in particular by reacting glucose or oligosaccharides with primary alcohols with 8 to 18 carbon atoms. With respect to the glycoside radical, both monoglycosides, in which a cyclic sugar radical is glycosidically bonded to the fatty alcohol, and oligomeric glycosides with a preferred degree of oligomerization of approximately 8 are suitable. Here, the degree of oligomerization is a statistical average value upon which a homolog distribution common for such technical products is based.

Partial Glycerides.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, as well as technical mixtures thereof, which can contain minor subordinate amounts of triglycerides from the production process. Addition products of 1 to 30, and preferably 5 to 10 mol of ethylene oxide onto the aforementioned partial glycerides are also suitable.

Sorbitan Esters.

Examples of suitable sorbitan esters include sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, as well as technical mixtures thereof. Addition products of 1 to 30, and preferably 5 to 10 mol of ethylene oxide onto the aforementioned sorbitan esters are also suitable.

Polyglycerol Esters.

Typical examples of suitable polyglycerol esters are polyglyceryl-2-dipolyhydroxystearate (Dehymuls® PGPH), polyglycerol-3-diisostearate (Lameform® TGI), polyglyceryl-4 isostearate (Isolan® GI 34), polyglyceryl-3 oleate, diisostearoyl polyglyceryl-3 diisostearate (Isolan®, PDI), polyglyceryl-3 methyl glucose distearate (Tego Care® 450), polyglyceryl-3 beeswax (Cera Bellina®), polyglyceryl-4 caprate (polyglycerol caprate T2010/90), polyglyceryl-3 cetyl ether (Chimexane® NL), polyglyceryl-3 distearate (Cremophor® GS 32) and polyglyceryl polyricinoleate (Admul® WOL 1403) polyglyceryl dimerate isostearate, and mixtures thereof. Examples of further suitable polyol esters, optionally reacted with 1 to 30 mol of ethylene oxide, are mono-, di- and triesters of trimethylolpropane or pentaerythritol with lauric acid, coconut fatty acid, tallow fatty acid, palmitic acid, stearic acid, oleic acid, behenic acid and the like.

Anionic Emulsifiers.

Typical anionic emulsifiers are aliphatic fatty acids with 12 to 22 carbon atoms, such as palmitic acid, stearic acid, or behenic acid, as well as dicarboxylic acids with 12 to 22 carbon atoms such as azelaic acid or sebacic acid.

Amphoteric and Cationic Emulsifiers.

In addition, zwitterionic surfactants may be used as emulsifiers. Zwitterionic surfactants are those surface-active compounds which bear at least one quaternary ammonium group and at least one carboxylate and one sulfonate group per molecule. Particularly suitable zwitterionic surfactants are the so-called betaines such as N-alkyl-N,N-dimethylammonium glycinates, for example cocoalkyl dimethylammonium glycinate, N-acylaminopropyl-N,N-dimethylammonium glycinates, for example cocoacylaminopropyl dimethylammonium glycinate, and 2-alkyl-3-carboxylmethyl-3-hydroxyethyl imidazolines, with in each case 8 to 18 carbon atoms in the alkyl or acyl group and cocoacylaminoethylhydroxyethylcarboxymethyl glycinate. Particularly preferred is the fatty acid amide derivative known by the CTFA name cocamidopropyl betaine. Ampholytic surfactants are also suitable emulsifiers. Ampholytic surfactants are understood to refer to those surface-active compounds which, in addition to one $C_{8/18}$-alkyl or acyl group per molecule, contain at least one free amino group and at least one —COOH or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids with in each case approx. 8 to 18 carbon atoms in the alkyl group. Particularly preferred ampholytic surfactants are N-cocoalkylaminopropionate, cocoacylaminoethylaminopropionate and $C_{12/18}$-acylsarcosine. Finally, cationic surfactants may also be considered as emulsifiers, with those of the esterquat type, preferably methyl-quaternized difatty acid triethanolamine ester salts, being particularly preferred.

Fats and Waxes

Typical examples of fats are glycerides, i.e. solid or liquid vegetable or animal products which consist essentially of mixed glycerol esters of higher fatty acids, suitable waxes include natural waxes, for example candelilla wax, carnauba wax, Japan wax, esparto grass wax, cork wax, guaruma wax, rice germ oil wax, sugarcane wax, ouricury wax, montan wax, beeswax, shellac wax, spermaceti, lanolin (wool wax), uropygial fat, ceresin, ozokerite (earth wax), petrolatum, paraffin waxes, microcrystalline waxes; chemically modified waxes (hard waxes), for example montan ester waxes, sasol waxes, hydrogenated jojoba waxes, and synthetic waxes, for example polyalkylene waxes and polyethylene glycol waxes. In addition to the fats, suitable additives are also fat-like substances such as lecithins and phospholipids. The term lecithins is understood by the person skilled in the art to refer to those glycerophospholipids which form from fatty acids, glycerol, phosphoric acid and choline by esterification. Lecithins are thus frequently also referred to as phosphatidylcholines (PC). Examples of natural lecithins which may be mentioned are the cephalins, which are also referred to as phosphatidic acids and represent derivatives of 1,2-diacyl-sn-glycerol-3-phosphoric acids. In contrast, phospholipids are usually understood to mean mono- and preferably diesters of phosphoric acid with glycerol (glycerophosphates), which are generally considered to be fats. In addition, sphingosines and sphingolipids are also suitable.

Pearlescent Waxes

Examples of suitable pearlescent waxes include: alkylene glycol esters, specifically ethylene glycol distearate; fatty acid alkanolamides, specifically coconut fatty acid diethanolamide; partial glycerides, specifically stearic acid monoglyceride; esters of polyvalent, optionally hydroxy-substituted carboxylic acids with fatty alcohols having 6 to 22 carbon atoms, specifically long-chain esters of tartaric acid; fatty substances, for example fatty alcohols, fatty ketones, fatty aldehydes, fatty ethers, and fatty carbonates which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Cooling Agents

Cooling agents are compounds which produce a cool feeling on the skin. As a rule, these are menthol compounds which—in addition to the parent substance menthol itself—are selected for example from the group composed of menthol methyl ether, menthone glyceryl acetal (FEMA GRAS[2] 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamate, monomethyl succinate (FEMA GRAS 3810), monomenthyl glutamate (FEMA GRAS 4006), menthoxy-1,2-propanediol (FEMA GRAS 3784), menthoxy-2-methyl-1,2-propanediol (FEMA GRAS 3849) as well as the menthane carboxylic acid esters and amides WS-3, WS-4, WS-5, WS-12, WS-14 and WS-30, and mixtures thereof.

[2]FEMA [text obscured] defined as "Generally Regarded As Safe" [text obscured] substance is tested according to a standard method and considered to be toxicologically safe.

A first important representative of these is monomenthyl succinate (FEMA GRAS 3810). Both the succinate and the analog monomenthyl glutarate (FEMA GRAS 4006) are important representatives of monomenthyl esters based on di- and poly-carboxylic acids:

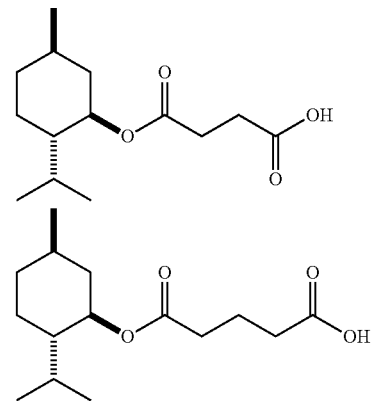

Examples of applications of these substances can be found for example in the documents WO 2003 043431 (Unilever) or EP 1332772 A1 (IFF).

The next important group of preferred menthol compounds according to the invention comprises carbonate esters of menthol and polyols such as glycols, glycerol, or carbohydrates such as menthol ethylene glycol carbonate (FEMA GRAS 3805=Frescolat® MGC), menthol propylene glycol carbonate (FEMA GRAS 3784=Frescolat®) MPC), menthol 2-methyl-1,2-propanediol carbonate (FEMA GRAS 3849), or the corresponding sugar derivatives. The menthol compounds menthyl lactate (FEMA GRAS 3748=Frescolat® ML), and in particular menthone glyceryl acetal (FEMA GRAS 3807) or menthone glyceryl ketal (FEMA GRAS 3808), which is marketed under the brand name Frescolat® MGA, are also preferred. Among these substances, menthone glyceryl acetal/ketal, menthyl lactate, and menthol ethylene glycol carbonate or menthol propylene glycol carbonate, which are marked by the applicant under the names Frescolat® MGA, Frescolat® ML, Frescolat® MGC, and Frescolat® MPC, have been found to be most particularly advantageous.

Menthol compounds, which have a C—C bond in the 3 position and also have a number of representatives suitable for use, were first developed in the 1970s. These are generally referred to as the WS type. The parent substance is a menthol derivative in which the hydroxyl group is replaced by a carboxyl group (WS-1). All other WS types are derived from this structure, such as the preferred species WS-3, WS-4, WS-5, WS-12, WS-14 and WS-30.

Bodying Agents and Thickeners

The main suitable bodying agents used are fatty alcohols or hydroxy fatty alcohols containing 12 to 22, and preferably 16 to 18, carbon atoms, as well as partial glycerides, fatty acids or hydroxy fatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil types (hydrophilic silicas), polysaccharides, in particular xanthan gum, guar-guar, agar-agar, alginates and tyloses, carboxymethylcellulose and hydroxyethyl and hydroxypropyl cellulose, also relatively high molecular weight polyethylene glycol monoesters and diesters of fatty acids, polyacrylates (for example, Carbopols® and Pemulen types from Goodrich; Synthalens® from Sigma; Keltrol types from Kelco; and Sepigel types from Seppic; Salcare types from Allied Colloids), polyacrylamides, polymers, polyvinyl alcohol and polyvinyl pyrrolidone. Other bodying agents which have proved to be particularly effective are bentonites, for example Bentonei Gel VS-5PC (Rheox) which is a mixture of cyclopentasiloxane, disteardimonium hectorite, and propylene carbonate. Other suitable bodying agents are surfactants such as ethoxylated fatty acid glycerides, esters of fatty acids with polyols such as pentaerythritol or trimethylol propane, narrow-range fatty alcohol ethoxylates or alkyl oligoglucosides, and electrolytes such as sodium chloride and ammonium chloride.

Superfatting Agents and Stabilizers

As superfatting agents, substances such as lanolin and lecithin, as well as polyethoxylated or acylated lanolin and lecithin derivatives, polyol fatty acid esters, monoglycerides and fatty acid alkanolamides may be used, with the latter also serving as foam stabilizers.

Metal salts of fatty acids, such as magnesium, aluminum and/or zinc stearate or ricinoleate, can be used as stabilizers.

Polymers

Suitable cationic polymers are, for example, cationic cellulose derivatives such as the quaternized hydroxyethyl cellulose obtainable from Amerchol under the name Polymer JR 400®, cationic starch, copolymers of diallyl ammonium salts and acrylamides, quaternized vinyl pyrrolidone/vinyl imidazole polymers such as Luviquat®, (BASF), condensation products of polyglycols and amines, quaternized collagen polypeptides such as lauryldimonium hydroxypropyl hydrolyzed collagen (Lamequat® L, Grünau), quaternized wheat polypeptides, polyethyleneimine, cationic silicone polymers such as amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as quaternized chitosan, optionally in microcrystalline distribution, condensation products of dihaloalkylenes such as dibromobutane with bis-dialkylamines, for example bis-dimethylamino-1,3-propane, cationic guar gum such as Jaguar® CBS, Jaguar® C-17, and Jaguar® C-16 from Celanese, and quaternized ammonium salt polymers such as Mirapol® A-15, Mirapol® AD-1, and Mirapol® AZ-1 from Miranol.

Examples of suitable anionic, zwitterionic, amphoteric, and nonionic polymers include vinyl acetate-crotonic acid copolymers, vinyl pyrrolidone-vinyl acrylate copolymers, vinyl acetate-butyl maleate-isobornyl acrylate copolymers, methyl vinyl ether-maleic anhydride copolymers and esters thereof, uncrosslinked and polyol-crosslinked polyacrylic acids, acrylamidopropyl trimethylammonium chloride-acrylate copolymers, octylacrylamide-methyl methacrylate-tert-butylaminoethyl methacrylate-2-hydroxypropyl methacrylate copolymers, polyvinyl pyrrolidone, vinyl pyrrolidone-vinyl acetate copolymers, vinyl pyrrolidone-dimethylaminoethyl methacrylate-vinyl caprolactam terpolymers, and optionally derivatized cellulose ethers and silicones.

Silicone Compounds

Examples of suitable silicone compounds are dimethyl polysiloxanes, methylphenyl polysiloxanes, cyclic silicones, and amino-, fatty acid-, alcohol-, polyether-, epoxy-, fluorine-, glycoside-, and/or allyl-modified silicone compounds, which may be both liquid and resin-like at room temperature. Other suitable silicone compounds are simethicones which are mixtures of dimethicones with an average chain length of 200 to 300 dimethylsiloxane units and hydrogenated silicates.

UV Protection Factors

UV protection factors are understood for example to be organic substances which are liquid or crystalline at room temperature (light protection filters) and are capable of absorbing ultraviolet radiation and then releasing the energy absorbed in the form of longer-wavelength radiation, for example, heat. UV protection factors are usually present in amounts of 0.1 to 5, and preferably 0.2 to 1 wt. UV-B filters can be oil-soluble or water-soluble. The following are examples of oil-soluble substances:

3-benzylidene camphor or 3-benzylidene norcamphor and the derivatives thereof, for example 3-(4-methylbenzylidene)-camphor;

4-aminobenzoic acid derivatives, preferably 4-(dimethylamino)benzoic acid-2-ethylhexyl ester, 4-(dimethylamino)benzoic acid-2-octyl ester, and 4-(dimethylamino)benzoic acid amyl ester;

cinnamic acid esters, preferably 4-methoxycinnamic acid-2-ethylhexyl ester, 4-methoxy-cinnamic acid propyl ester, 4-methoxycinnamic acid isoamyl ester, and 2-cyano-3,3-phenylcinnamic acid-2-ethylhexyl ester (octocrylene);

salicylic acid esters, preferably salicylic acid-2-ethylhexyl ester, salicylic acid-4-iso-propylbenzyl ester, and salicylic acid homomenthyl ester;

derivatives of benzophenone, preferably 2-hydroxy-4-methoxybenzophenone, 2-hydroxy-4-methoxy-4'-methylbenzophenone, and 2,2'-dihydroxy-4-methoxybenzophenone;

benzalmalonic acid esters, preferably 4-methoxybenzalmalonic acid di-2-ethylhexyl ester;

triazine derivatives such as 2,4,6-trianilino-(p-carbo-2'-ethyl-1'-hexyloxy)-1,3,5-triazine and octyl triazone or dioctyl butamidotriazone (UvasorbC HEB);

propan-1,3-diones such as 1-(4-tert-butylphenyl)-3-(4'methoxyphenyl)propan-1,3-dione; and ketotricyclo(5.2.1.0)decane derivatives.

Suitable water-soluble substances include:

2-phenylbenzimidazol-5-sulfonic acid and alkali metal, alkaline earth metal, ammonium, alkylammonium, alkanolammonium, and glucammonium salts thereof;

1H-benzimidazole-4,6-disulfonic acid, 2,2'-(1,4-phenylene)bis-disodium salt (Neo Heliopan® AP);

sulfonic acid derivatives of benzophenones, preferably 2-hydroxy-4-methoxybenzophenone-5-sulfonic acid and salts thereof;

sulfonic acid derivatives of 3-benzylidene camphor such as 4-(2-oxo-3-bornylidenemethyl)-benzene sulfonic acid and 2-methyl-5-(2-oxo-3-bornylidene)-sulfonic acid and salts thereof.

Particular examples of typical UV-A filters include derivatives of benzoyl methane such as 1-(4'-tert-butylphenyl)-3-(4'-methoxyphenyl)-propane-1,3-dione, 4-tert-butyl-4'-methoxydibenzoyl methane (Parsol®: 1789), 2-(4-diethylamino-2-hydroxybenzoyl)-benzoic acid hexyl ester (Uvinul® A Plus), 1-phenyl-3-(4'-isopropylphenyl)-propane-1,3-dione, and enamine compounds. The UV-A and UV-B filters may of course also be used in the form of mixtures. Particularly favorable combinations consist of the derivatives of benzoyl methane, for example 4-tert-butyl-4'-methoxydibenzoyl methane (Parsol® 1789) and 2-cyano-3,3-phenylcinnamic acid-2-ethyl hexyl ester (octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Such combinations are advantageously combined with water-soluble filters such as 2-phenylbenzimidazole-5-sulfonic acid and alkali metal, alkaline earth metal, ammonium, alkylammonium, alkanolammonium and glucammonium salts thereof.

In addition to the soluble substances mentioned above, insoluble light-blocking pigments, i.e. finely dispersed metal oxides or salts, may also be used for this purpose. Examples of suitable metal oxides are, in particular, zinc oxide and titanium dioxide, as well as oxides of iron, zirconium oxide, silicon, manganese, aluminum and cerium and mixtures thereof. Silicates (talcum), barium sulfate, or zinc stearate may be used as salts. The oxides and salts are used in the form of the pigments for skin-care and skin-protecting emulsions and decorative cosmetics. The particles should have a mean diameter of less than 100 nm, preferably 5 to 50 nm, and more preferably 15 to 30 nm. They may be spherical in shape, but particles having an ellipsoid shape or deviating in any other way from a spherical shape may also be used. The pigments may also be surface-treated, i.e. hydrophilized or hydrophobized. Typical examples are coated titanium dioxides, for example Titanium Dioxide T 805 (Degussa) and Eusolex® T2000, Eusolex® T, Eusolex® T-ECO, Eusolex® T-S, Eusolex® T-Aqua, Eusolex®-T-45D (all from Merck), and Uvinul TiO$_2$ (BASF). Suitable hydrophobic coating materials are above all silicones, and among these, especially trialkoxyoctylsilanes or simethicones. So-called micro- or nanopigments are preferably used in sun protection products. Micronized zinc oxide such as Z-COTE® or Z-COTE HP1® is preferably used.

Humectants

Humectants are used to further optimize the sensory properties of the composition and for moisture regulation of the skin. At the same time, the low-temperature stability of the preparations according to the invention, in particular in the case of emulsions, is increased. Humectants are ordinarily contained in an amount of 0.1 to 15 wt %, preferably 1 to 10 wt %, and in particular 5 to 10 wt %.

Suitable humectants according to the invention include amino acids, pyrrolidone carboxylic acid, lactic acid and salts thereof, lactitol, urea and urea derivatives, uric acid, glucosamine, creatinine, decomposition products of collagen, chitosan or chitosan salts/derivatives, and in particular polyols and polyol derivatives (e.g. glycerol, diglycerol, triglycerol, ethylene glycol, propylene glycol, butylene glycol, erythritol, 1,2,6-hexanetriol, polyethylene glycols such as PEG-4, PEG-6, PEG-7, PEG-8, PEG-9, PEG-10, PEG-12, PEG-14, PEG-16, PEG-18, and PEG-20), sugar and sugar derivatives (such as fructose, glucose, maltose, maltitol, mannitol, inositol, sorbitol, sorbityl silanediol, sucrose, trehalose, xylose, xylitol, glucuronic acid and salts thereof), ethoxylated sorbitol (sorbeth-6, sorbeth-20, sorbeth-30, sorbeth-40), honey and hydrogenated honey, and hydrogenated starch hydrolysate, as well as mixtures of hardened wheat protein and PEG-20 acetate copolymer. According to the invention, particularly suitable humectants are glycerol, diglycerol, triglycerol, and butylene glycol.

Biogenic Active Ingredients and Antioxidants

Biogenic active ingredients are understood to refer, for example, to tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts such as prune extract and bambaranus extract, and vitamin complexes.

Antioxidants interrupt the photochemical reaction chain triggered when UV radiation penetrates the skin. Typical examples are amino acids (e.g. glycine, histidine, tyrosine, tryptophan) and the derivatives thereof, imidazole (e.g. urocanic acid) and the derivatives thereof, peptides such as D,L-carnosine, D-carnosine, L-carnosine and the derivatives thereof (e.g. anserine), carotenoids, carotenes (e.g. α-carotene, β-carotene, lycopene) and the derivatives thereof, chlorogenic acid and the derivatives thereof, lipoic acid and the derivatives thereof (such as dihydrolipoic acid), aurothioglucose, propylthiouracil and other thiols (such as thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl, and glyceryl esters thereof) and the salts thereof, dilauryl thiodipropionate, distearyl thiodipropionate, thiodipropionic acid and the derivatives thereof (esters, ethers, peptides, lipids, nucleotides, nucleosides and salts) and sulfoximine compounds (such as buthionine sulfoximine, homocysteine sulfoximine, buthionine sulfones, and penta-, hexa-, heptathionine sulfoximine) in very small compatible doses (such as pmol to pmol/kg), also (metal) chelating agents (such as α-hydroxy fatty acids, palmitic acid, phytic acid, lactoferrin), α-hydroxy acids (such as citric acid, lactic acid, malic acid), humic acid, bile acid, bile extracts, bilirubin, biliverdin, EDTA, EGTA and the derivatives thereof, unsaturated fatty acids and the derivatives thereof (such as γ-linolenic acid, linoleic acid, oleic acid), folic acid and the derivatives thereof, ubiquinone and ubiquinol and the derivatives thereof, vitamin C and derivatives (such as ascorbyl palmitate, Mg ascorbyl phosphate, ascorbyl acetate), tocopherols and derivatives (such as vitamin E acetate), vitamin A and derivatives (vitamin A palmitate) as well as coniferyl benzoate of benzoic resin, rutinic acid and the derivatives thereof, α-glycosyl rutin, ferulic acid, furfurylidene glucitol, carnosine, butylhydroxytoluene, butylhydroxyanisole, nordihydroguaiac resin acid, nordihydroguaiaretic acid, trihydroxybutyrophenone, uric acid and the derivatives thereof, mannose and the derivatives thereof, superoxide dismutase, zinc and the derivatives thereof (such as ZnO, $ZnSO_4$), selenium and the derivatives thereof (such as selenium methionine), stilbenes and the derivatives thereof (such as stilbene oxide, trans-stilbene oxide) and derivatives suitable according to the invention (salts, esters, ethers, sugars, nucleotides, nucleosides, peptides and lipids) of these active ingredients.

Deodorants and Antimicrobial Agents

Cosmetic deodorants (odor inhibitors) counteract, mask, or eliminate body odors. Body odors result from the action of skin bacteria on apocrine perspiration, causing the formation of decomposition products having an unpleasant odor. Accordingly, deodorants contain active ingredients that function as antimicrobial agents, enzyme inhibitors, odor absorbers, or odor-masking agents.

Antimicrobial Agents.

Suitable antimicrobial agents are, in principle, all substances effective against gram-positive bacteria, for example 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), and salicylic acid N-alkylamides, for example n-octylsalicylamide or n-decylsalicylamide.

Enzyme inhibitors. Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing odor formation. Other substances which are suitable esterase inhibitors are sterol sulfates or phosphates, for example lanosterol, cholesterol, campesterol, stigmasterol and sitosterol sulfate or phosphate, dicarboxylic acids and esters thereof, for example glutaric acid, monoethyl glutarate, diethyl glutarate, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate.

Odor Absorbers.

Suitable as odor absorbers are substances which can absorb and largely retain odor-forming compounds. They lower the partial pressure of the individual components and thus also reduce their rate of propagation. It is important that perfumes remain unaffected thereby. Odor absorbers are not effective against bacteria. They contain as their main constituent, for example, a complex zinc salt of ricinoleic acid or specific, largely odor-neutral fragrances, which are known to the person skilled in the art as "fixatives", such as extracts of labdanum oil or styrax oil or certain abietic acid derivatives. Fragrances or perfume oils, which in addition to their function as odor-masking agents impart their respective scent note to deodorants, function as odor-masking agents. Examples of perfume include mixtures of natural and synthetic fragrances. Natural fragrances are extracts of flowers, stems and leaves, fruits, fruit peels, roots, woods, herbs and grasses, needles and branches, as well as resins and balsams. Also suitable are animal raw materials, for example civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, clove oil, melissa oil, mint oil, cinnamon leaf oil, linden flower oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix Coeur, iso-E-super, Fixolide NP, evernyl, iraldein gamma, phenylacetic acid, geranyl acetate, benzyl acetate, rose oxide, Romilat, Irotyl and Floramat alone or in mixtures.

Antiperspirants.

Antiperspirants (perspiration inhibitors) reduce the formation of perspiration by affecting the activity of the eccrine sweat glands, thus counteracting armpit wetness and body odor. Aqueous or water-free formulations of antiperspirants typically contain the following ingredients:
  astringent active ingredients,
  oil components,
  nonionic emulsifiers,
  coemulsifiers,
  bodying agents,
  auxiliaries such as thickeners or complexing agents, and/or
  nonaqueous solvents such as ethanol, propylene glycol and/or glycerol.

Suitable astringent antiperspirant active ingredients are primarily salts of aluminum, zirconium or zinc. Such suitable antihydrotic active ingredients include aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids such as glycine. In addition, customary oil-soluble and water-soluble auxiliaries may be present in antiperspirants in relatively small amounts. Examples of such oil-soluble auxiliaries are:
- anti-inflammatory, skin-protective, or perfumed ethereal oils,
- synthetic skin-protective active ingredients, and/or
- oil-soluble perfume oils.

Common water-soluble additives include preservatives, water-soluble fragrances, pH adjusting agents, e.g. buffer mixtures, water-soluble thickeners, e.g. water-soluble natural or synthetic polymers such as xanthan gum, hydroxyethylcellulose, polyvinylpyrrolidone, or high-molecular polyethylene oxide.

Film-Forming Agents

Common film-forming agents include chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid or salts thereof, and similar compounds.

Antidandruff Active Ingredients

Examples of suitable antidandruff active ingredients are piroctone olamine (1-hydroxy-4-methyl-6-(2,4,4-trimethylpentyl)-2-(1H)-pyridinone monoethanolamine salt), Baypival® (climbazole), Ketoconazole®, (4-acetyl-1-{-4-[2-(2, 4-dichlorophenyl) r-2-(1H-imidazol-1-ylmethyl)-1,3-dioxylan-c-4-ylmethoxyphenyl}piperazine, ketoconazole, elubiol, selenium disulfide, colloidal sulfur, sulfur polyethylene glycol sorbitan monooleate, sulfur ricinol polyethoxylate, sulfur tar distillates, salicylic acid (or in combination with hexachlorophene), undecylenic acid monoethanolamide sulfosuccinate Na salt, Lamepon. UD (protein-undecylenic acid condensate), zinc pyrithione, aluminum pyrithione and magnesium pyrithione/dipyrithione magnesium sulfate.

Swelling Agents

Swelling agents for aqueous phases may be montmorillonites, clay minerals, Pemulen, and alkyl-modified Carbopol grades (Goodrich). Further suitable polymers or swelling agents are given in the overview by R. Lochhead in Cosm. Toil. 108, 95 (1993).

Insect Repellents

Examples of suitable insect repellents include N,N-diethyl-m-toluamide, 1,2-pentanediol, or ethyl butylacetylaminopropionate. A suitable self-tanning agent is dihydroxyacetone. Examples of suitable tyrosine inhibitors, which prevent the formation of melanin and are used in depigmenting agents, include arbutin, ferulic acid, kojic acid, coumaric acid, and ascorbic acid (vitamin C).

Ingredients for Oral and Dental Care Compositions

Oral and dental care compositions are understood to be products used for cleaning and care of the mouth and teeth. Examples are toothpastes, tooth gels, and the like.

Toothpastes or dental creams are generally understood to be gel-like or pasty preparations made from water, thickeners, humectants, abrasive or cleaning agents, surfactants, sweeteners, flavorings, deodorizing active ingredients, as well as active ingredients to combat oral and dental diseases. In the toothpastes according to the invention, all commonly-used cleaning agents, such as chalk, dicalcium phosphate, insoluble sodium metaphosphate, aluminum silicates, calcium pyrophosphate, fine particulate synthetic resins, silicic acids, aluminum oxide, and aluminum oxide trihydrate can be used.

Preferably suitable cleaning agents for the toothpastes according to the invention are primarily fine particulate silica xerogels, silica hydrogels, precipitated silicas, aluminum oxide trihydrate and fine particulate α-aluminum oxide or mixtures of these cleaning agents in amounts of 15 to 40 wt % of the toothpaste. Suitable humectants are predominantly low molecular weight polyethylene glycols, glycerol, sorbitol or mixtures of these products in amounts up to 50 wt %. Among the known thickeners, the thickening, fine particulate silica gels and hydrocolloids, such as carboxymethylcellulose, hydroxyethylcellulose, hydroxypropyl guar, hydroxyethyl starch, polyvinylpyrrolidone, high molecular weight polyethylene glycol, plant gums such as tragacanth, agar agar, carrageenan moss, gum arabic, xanthan gum, and carboxyvinyl polymers (e.g. Carbopol® grades) are suitable. In addition to the mixtures of menthofuran and menthol compounds, the oral and dental care compositions can in particular comprise surface-active substances, preferably anionic and nonionic high-foaming surfactants such as the substances already listed above, but in particular alkyl ether sulfate salts, alkyl polyglucosides, and mixtures thereof.

Further common toothpaste additives are:
- preservatives and antimicrobial substances such as p-hydroxybenzoic acid methyl, ethyl or propyl ester, sodium sorbate, sodium benzoate, bromochlorophen, phenylsalicylic acid esters, thymol and the like;
- antitartar active ingredients, e.g. organophosphates such as 1-hydroxyethane-1,1-diphosphonic acid, 1-phosphonopropane-1,2,3-tricarboxylic acid, and others, which are known for example from U.S. Pat. No. 3,488,419, DE 2224430 A1 and DE 2343196 A1;
- other caries-inhibiting substances such as sodium fluoride, sodium monofluorophosphate, and stannous fluoride;
- sweeteners, such as sodium saccharin, sodium cyclamate, sucrose, lactose, maltose, fructose, or Aspartame®, (L-aspartyl-L-phenylalanine methyl ester), Stevia extracts, or sweetening components thereof, in particular ribeaudioside;
- additional flavoring agents such as eucalyptus oil, anise oil, fennel oil, cumin oil, methyl acetate, cinnamaldehyde, anethole, vanillin, and thymol, as well as mixtures of these and other natural and synthetic flavoring agents;
- pigments such as titanium dioxide;
- dyes;
- buffer substances such as primary, secondary or tertiary alkali metal phosphates, or citric acid/sodium citrate; and
- wound-healing and anti-inflammatory substances such as allantoin, urea, azulene, chamomile active ingredients, and acetylsalicylic acid derivatives.

A preferred embodiment of the cosmetic preparations is toothpastes in the form of an aqueous, pasty dispersion comprising polishing agents, humectants, viscosity regulators, and optionally further common components, as well as the mixture of menthofuran and menthol compounds in amounts of 0.5 to 2 wt %.

In order to improve flow behavior, hydrotropes such as ethanol, isopropyl alcohol, or polyols can also be used; these substances largely correspond to the carriers described above. Polyols that are suitable here preferably have 2 to 15 carbon atoms and at least two hydroxyl groups. The polyols can also contain further functional groups, in particular amino groups, or be modified with nitrogen. Typical examples are
- glycerol;
- alkylene glycols such as ethylene glycol, diethylene glycol, propylene glycol, butylene glycol, hexylene glycol, and polyethylene glycols with an average molecular weight of 100 to 1000 daltons;

technical-grade oligoglycerol mixtures with an intrinsic degree of condensation of 1.5 to 10, such as technical-grade diglycerol mixtures with a diglycerol content of 40 to 50 wt %;

methyol compounds, such as in particular trimethylolethane, trimethylolpropane, trimethylolbutane, pentaerythritol and dipentaerythritol;

low alkyl glycosides, in particular those having 1 to 8 carbon atoms in the alkyl radical, such as methyl and butyl glycoside;

sugar alcohols having 5 to 12 carbon atoms, such as sorbitol or mannitol;

sugars with 5 to 12 carbon atoms, such as glucose or saccharose;

amino sugars, such as glucamine; and dialcohol amines, such as diethanolamine or 2-amino-1,3-propanediol.

Examples of suitable preservatives include phenoxyethanol, formaldehyde solution, parabens, pentanediol or sorbic acid, the silver complexes known under the name Surfacine®, and the other classes of substance listed in Annex 6, Part A and B of the Cosmetics Ordinance.

Perfume oils that may be mentioned are mixtures of natural and synthetic fragrances. Natural fragrances are extracts from flowers (lily, lavender, rose, jasmine, neroli, ylang ylang), stems and leaves (geranium, patchouli, petitgrain), fruits (anise, coriander, cumin, juniper), fruit peels (bergamot, lemon, orange), roots (maize, angelica, celery, cardamom, costus, iris, calmus), woods (pinewood, sandalwood, guaiac wood, cedar wood, rosewood), herbs and grasses (tarragon, lemon grass, sage, thyme), needles and branches (spruce, fir, pine, dwarf-pine), and resins and balsams (galbanum, elemi, benzoe, myrrh, olibanum, opoponax). Animal raw materials such as civet and castoreum are also suitable. Typical synthetic fragrance compounds are products of the ester, ether, aldehyde, ketone, alcohol and hydrocarbon types. Fragrance compounds of the ester type include benzyl acetate, phenoxyethyl isobutyrate, p-tert-butyl cyclohexyl acetate, linalyl acetate, dimethyl benzyl carbinyl acetate, phenylethyl acetate, linalyl benzoate, benzyl formate, ethyl methylphenyl glycinate, allyl cyclohexylpropionate, styrallyl propionate and benzyl salicylate. The ethers include benzyl ethyl ethers, the aldehydes include linear alkanals having 8 to 18 carbon atoms, citral, citronellal, citronellyloxyacetaldehyde, cyclamen aldehyde, hydroxycitronellal, lilial and bourgeonal, the ketones include the ionones, α-isomethyl ionone and methyl cedryl ketone, the alcohols include anethole, citronellol, eugenol, isoeugenol, geraniol, linalool, phenylethyl alcohol and terpineol, and the hydrocarbons include primarily the terpenes and balsams. Preferably, however, preference mixtures of different fragrances which together produce a pleasant scent note are used. Essential oils of lower volatility, which are mostly used as fragrance components, are also suitable as perfume oils, e.g. sage oils, camellia oil, clove oil, melissa oil, mint oil, cinnamon leaf oil, linden blossom oil, juniper berry oil, vetiver oil, olibanum oil, galbanum oil, labolanum oil, and lavandin oil. Preferably, bergamot oil, dihydromyrcenol, lilial, lyral, citronellol, phenylethyl alcohol, α-hexylcinnamaldehyde, geraniol, benzyl acetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix Coeur, iso-E-Super, Fixolide NP, evernyl, iraldein gamma, phenylacetic acid, geranyl acetate, benzyl acetate, rose oxide, Romilat, Irotyl and Floramat are used alone or in mixtures.

Examples of suitable flavoring agents include peppermint oil, spearmint oil, anise oil, star anise oil, cumin oil, eucalyptus oil, fennel oil, lemon oil, wintergreen oil, clove oil, menthol and the like.

Hydrotropes

In order to improve flow behavior, hydrotropes such as ethanol, isopropyl alcohol, or polyols can be used; these substances largely correspond to the carriers specified above. Polyols which are suitable here preferably have 2 to 15 carbon atoms and at least two hydroxyl groups. The polyols can also contain further functional groups, in particular amino groups, or be modified with nitrogen. Typical examples are:

glycerol;

alkylene glycols, such as ethylene glycol, diethylene glycol, propylene glycol, butylene glycol, hexylene glycol, and polyethylene glycols with an average molecular weight of 100 to 1000 daltons;

technical-grade oligoglycerol mixtures with an intrinsic degree of condensation of 1.5 to 10 such as technical-grade diglycerol mixtures with a diglycerol content of 40 to 50 wt %;

methylol compounds, such as in particular trimethylolethane, trimethylolpropane, trimethylol-butane, pentaerythritol, and dipentaerythritol;

lower alkyl glucosides, in particular those with 1 to 8 carbon atoms in the alkyl radical, such as methyl and butyl glucoside;

sugar alcohols with 5 to 12 carbon atoms, such as sorbitol or mannitol, sugars with 5 to 12 carbon atoms, such as glucose or saccharose;

amino sugars such as glucamine; and dialcohol amines, such as diethanolamine or 2-amino-1,3-propanediol.

Preservatives

Examples of suitable preservatives include phenoxyethanol, formaldehyde solution, parabens, pentanediol, or sorbic acid as well as the silver complexes known under the name Surfacine® and the other classes of substance listed in Annex 6, Part A and B of the Cosmetics Directive.

Perfume Oils, Flavoring Agents, Flavorings, Fragrances

Preferably, the fragrances and perfume oils used are not subject to any restrictions whatsoever. It is therefore possible to use as fragrances individual fragrance compounds, either synthetic or natural compounds of the class of esters, ethers, aldehydes, ketones, alcohols, hydrocarbons, acids, carbonic esters, aromatic hydrocarbons, aliphatic hydrocarbons, saturated and/or unsaturated hydrocarbons, and mixtures thereof. The fragrance aldehydes or fragrance ketones used may be all common fragrance aldehydes and fragrance ketones typically used to produce a pleasant fragrance sensation. Suitable fragrance aldehydes and fragrance ketones are commonly known to the person skilled in the art. The fragrance ketones may comprise all ketones which are able to impart a desired fragrance or a sensation of freshness. Mixtures of different ketones may also be used. For example, the ketone may be selected from the group consisting of Buccoxime, isojasmone, methyl β-naphthyl ketone, musk indanone, Tonalid/musk plus, α-damascone, β-damascone, δ-damascone, isodamascone, damascenone, damarose, methyl dihydrojasmonate, menthone, carvone, camphor, fenchone, α-ionone, β-ionone, dihydro-β-ionone, γ-methyl so-called ionone, fleuramone, dihydrojasmone, cisjasmone, Iso-E-Super, methyl cedrenyl ketone or methyl cedrylone, acetophenone, methyl acetophenone, para-methoxyacetophenone, methyl β-naphthyl ketone, benzylacetone, benzophenone, para-hydroxyphenylbutanone, celery ketone or Livescone, 6-isopropyldecahydro-2-naphthone, dimethyloctenone, Freskomenthe, 4-(1-ethoxyvinyl)-3,3,5,5-tetramethyl cyclohexanone, methyl heptenone, 2-(2-(4-methyl-3-cyclohexen-1-yl)propyl)cyclopentanone, 1-(p-menthen-6(2)-yl)-1-propanone, 4-(4-hydroxy-3-methoxyphenyl)-2-butanone, 2-acetyl-3,3-dimethyl norbornane, 6,7-dihydro-1,1,2,3,3-pentamethyl-4(5H)-indanone, 4-damascol, dulcinyl or cassione, gelsone, hexalone, isocyclemone E, methyl cyclocitrone, methyl lavender ketone, orivone, para-tert-butylcyclohexanone, verdone, delphone, muscone, neobutenone, plicatone, veloutone, 2,4,4,7-tetramethyloct-6-en-3-one, tetramerane, hedione and mixtures thereof. The ketones may preferably be selected from α-damascone, 6-damascone, isodamascone, carvone, γ-methyl ionone, Iso-E-Super, 2,4,4,7-tetramethyloct-6-en-3-one, benzyl acetone, β-damascone, damascenone, methyl dihydrojasmonate, methyl cedrylone, hedione and mixtures thereof.

Suitable fragrance aldehydes may be any aldehydes that provide a desired fragrance or feeling of freshness corresponding to the fragrance ketones. However, they can also be individual aldehydes or aldehyde mixtures. Suitable aldehydes are for example melonal, triplal, ligustral, adoxal, anisaldehyde, cymal, ethyl vanillin, florhydral, floralozone, helional, heliotropin, hydroxycitronellal, koavone, Laurin aldehyde, canthoxal, lyral, lilial, adoxal, anisaldehyde, cumal methylnonyl acetaldehyde, citronellal, citronellyl oxyacetaldehyde, cyclamene aldehyde, bourgeonal, p,t-bucinal, phenylacetaldehyde, undecylenic aldehyde, vanillin; 2,6,10-trimethyl-9-undecenal, 3-dodecen-1-al, α-n-amylcinnamaldehyde, 4-methoxybenzaldehyde, benzaldehyde, 3-(4-tert-butylphenyl)-propanal, 2-methyl-3-(paramethoxyphenylpropanal), 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropyl-benzaldehyde, 1,2,3,4,5,6,7,8-octahydro-8,8-dimethyl-2-naphthaldehyde,2,4-dimethyl-3-cyclohexene-1-carboxyaldehyde, 2-methyl-3-(isopropyl phenyl)propanal, decyl aldehyde, 2,6-dimethyl-5-heptenal; 4-(tricyclo[5.2.1.0(2,6)]-decylidene-8)-butanal; octahydro-4,7-methano-1H-indene carboxaldehyde; 3-ethoxy-4-hydroxybenzaldehyde, para-ethyl-α,α-dimethylhydrocinnamaldehyde, α-methyl-3,4-(methylene dioxy)-hydrocinnamaldehyde, 3,4-methylene dioxybenzaldehyde, α-n-hexylcinnamaldehyde, m-cymene-7-carboxaldehyde, α-methyl phenylacetaldehyde, 7-hydroxy-3,7-dimethyl octanal, undecenal, 2,4,6-trimethyl-3-cyclohexene-1-carboxaldehyde, 4-(3)(4-methyl-3-pentenyl)-3-cyclohexene carboxaldehyde, 1-dodecanal, 2,4-dimethylcyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, 3-(4-ethylphenyl)-2,2-dimethylpropanal, 3-(4-methoxyphenyl)-2-methylpropanal, methyl nonylacetaldehyde, 2-phenylpropan-1-al, 3-phenylprop-2-en-1-al, 3-phenyl-2-pentylprop-2-en-1-al, 3-phenyl-2-hexylprop-2-enal, 3-(4-isopropyl phenyl)-2-methylpropan-1-al, 3-(4-ethylphenyl)-2,2-dimethylpropan-1-al, 3-(4-tert-butylphenyl)-2-methylpropanal, 3-(3,4-methylendioxy-phenyl)-2-methylpropan-1-al, 3-(4-ethylphenyl)-2,2-dimethylpropanal, 3-(3-isopropyl phenyl)-butan-1-al, 2,6-dimethylhept-5-en-1-al, dihydrocinnamaldehyde, 1-methyl-4-(4-methyl-3-pentenyl)-3-cyclohexene-1-carboxaldehyde, 5 or 6 methoxyhexahydro-4,7-methanoindan-1 or 2-carboxyaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexene-carboxyaldehyde, 7-hydroxy-3,7-dimethyloctanal; trans-4-decenal, 2,6-nonadienal, para-tolylacetaldehyde; 4-methylphenylacetaldehyde, 2-methyl-4-(2,6,6-trimethyl-1-cyclohexen-1-yl)-2-butenal, ortho-methoxycinnamaldehyde, 3,5,6-trimethyl-3-cyclohexene carboxaldehyde, 3,7-dimethyl-2-methylene-6-octenal, phenoxyacetaldehyde; 5,9-dimethyl-4,8-decadienal, peony aldehyde (6,10-dimethyl-3-oxa-5,9-undecadien-1-al), hexahydro-4,7-methanoindan-1-carboxaldehyde, octanal, 2-methyl octanal, α-methyl-4-(1-methylethyl)benzene acetaldehyde, 6,6-dimethyl-2-norpinene-2-propionaldehyde, paramethyl phenoxyacetaldehyde, 2-methyl-3-phenyl-2-propen-1-al, 3,5,5-trimethylhexanal, hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methyl nonyl acetaldehyde, 1-p-menthene-q-carboxaldehyde, citral or mixtures thereof, lilial citral, 1-decanal, n-undecanal, n-dodecanal, florhydral, 2,4-dimethyl-3-cyclohexene-1-carboxaldehyde 4-methoxybenzaldehyde, 3-methoxy-4-hydroxybenzaldehyde, 3-ethoxy-4-hydroxybenzaldehyde, 3,4-methylene dioxybenzaldehyde, and 3,4-dimethoxybenzaldehyde and mixtures thereof. As mentioned in the above examples, the fragrance aldehydes and fragrance ketones can have an aliphatic, cycloaliphatic, aromatic, ethylenically unsaturated structure or a combination of these structures. Moreover, there may also be further heteroatoms or polycyclic structures. The structures can have suitable substituents such as hydroxyl or amino groups. For further suitable fragrances selected from aldehydes and ketones, reference is made to "Steffen Arctander, published 1960 and 1969 respectively, reprinted 2000 ISBN: Aroma Chemicals Vol. 1: 0-931710-37-5, Aroma Chemicals Vol. 2: 0-931710-38-3".

Examples of suitable fragrance compounds of the ester type include benzyl acetate, phenoxyethyl isobutyrate, p-tert-butylcyclohexyl acetate, linalyl acetate, dimethylbenzyl carbinyl acetate (DMBCA), phenylethyl acetate, benzyl acetate, ethyl methyl phenylglycinate, allyl cyclohexyl propionate, styrallyl propionate, benzyl salicylate, cyclohexyl salicylate, floramat, melusat, and jasmacyclate. Examples of fragrance compounds of the hydrocarbon type include terpenes such as limonene and pinene. Examples of suitable fragrances of the ether type include benzyl ethyl ether and ambroxan. Examples of suitable fragrance alcohols include 10-undecen-1-ol, 2,6-dimethylheptan-2-ol, 2-methyl butanol, 2-methyl pentanol, 2-phenoxyethanol, 2-phenyl propanol, 2-tert-butyl cyclohexanol, 3,5,5-trimethyl cyclohexanol, 3-hexanol, 3-methyl-5-phenyl pentanol, 3-octanol, 1-octen-3-ol, 3-phenyl propanol, 4-heptenol, 4-isopropyl cyclohexanol, 4-tert-butyl cyclohexanol, 6,8-dimethyl-2-nonanol, 6-nonen-1-ol, 9-decen-1-ol, α-methylbenzyl alcohol, α-terpineol, amyl salicylate, benzyl alcohol, benzyl salicylate, β-terpineol, butyl salicylate, citronellol, cyclohexyl salicylate, decanol, dihydromyrcenol, dimethylbenzyl carbinol, dimethyl heptanol, dimethyl octanol, ethyl salicylate, ethylvanilin, anethol, eugenol, geraniol, heptanol, hexyl salicylate, isoborneol, isoeugenol, isopulegol, linalool, menthol, myrtenol, n-hexanol, nerol, nonanol, octanol, para-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, and cinnamyl alcohol, and if a plurality of fragrance alcohols are present, they may be selected independently of one another.

Fragrances or perfume oils can also be natural fragrance mixtures, such as those obtainable from plant sources, e.g. pine, citrus, jasmine, patchouli, rose or ylang-ylang oil. Also suitable are clary sage oil, camomile oil, clove oil, balm oil, mint oil, cinnamon leaf oil, lime blossom oil, juniper berry oil, vetiver oil, olibanum oil, galbanum oil and labdanum oil, and also orange blossom oil, neroli oil, orange peel oil and sandalwood oil. Essential oils such as angelica root oil, aniseed oil, arnica blossom oil, basil oil, bay oil, champaca flower oil, silver fir oil, silver fir cone oil, elemi oil, eucalyptus oil, fennel oil, pine needle oil, galbanum oil, geranium oil, gingergrass oil, guaiac wood oil, gurjan balsam oil, helichrysum oil, ho oil, ginger oil, iris oil, cajeput oil, sweet flag oil, camomile oil, camphor oil, cananga oil, cardamom oil, cassia oil, pine needle oil, copaiba balsam oil, coriander oil, spearmint oil, caraway oil, cumin oil, lavender oil, lemongrass oil, lime oil, mandarin oil, melissa oil, amber seed oil, myrrh oil, clove oil, neroli oil, niaouli oil, olibanum oil, oregano oil, palmarosa oil, patchouli oil, peru balsam oil, petitgrain oil, pepper oil, peppermint oil, pimento oil, pine oil, rose oil, rosemary oil, sandalwood oil, celery oil, spike oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, citrus oil, and cypress oil.

So-called fragrance precursors (pro-drugs) are also suitable as fragrant substances. This class of compounds comprises compounds which release a desired odor molecule and/or fragrance molecule through the breaking of a chemical bond, by hydrolysis, for example. In order to form a fragrance precursor, a desired fragrance raw material is typically joined chemically to a carrier, preferably a carrier of low or moderate volatility. The combination results in a less volatile and more strongly hydrophobic fragrance precursor, with better attachment to materials. The fragrance is released subsequently by breaking of the bond between the fragrance raw material and the carrier, as a result of the change in pH, for example (through perspiration during wear, for example), atmospheric humidity, heat and/or sunlight during storage or drying on a clothesline.

The fragrance raw material for use in fragrance precursors typically comprises saturated or unsaturated volatile compounds containing an alcohol, an aldehyde and/or a ketone group. The fragrance raw materials that are useful herein include any pleasingly fragrant substances or mixtures of substances which have already been described above.

Particularly advantageous fragrance precursors which can be used conform to Formula (III)

$$R—C(OR^1)(OR^2)—OR^3 \quad (III)$$

where R denotes hydrogen, linear $C_1$-$C_8$ alkyl, branched $C_3$-$C_{20}$ alkyl, cyclic $C_3$-$C_{20}$ alkyl, branched cyclic $C_6$-$C_{20}$ alkyl, linear $C_6$-$C_{20}$ alkenyl, branched $C_6$-$C_{20}$ alkenyl, cyclic $C_6$-$C_{20}$ alkenyl, branched cyclic $C_6$-$C_{20}$ alkenyl, substituted or unsubstituted $C_6$-$C_{20}$ aryl and mixtures thereof; $R^1$, $R^2$ and $R^3$ independently are linear, branched, or substituted $C_1$-$C_{20}$ alkyl; linear, branched or substituted $C_2$-$C_{20}$ alkenyl; substituted or unsubstituted cyclic $C_3$-$C_{20}$ alkyl; substituted or substituted $C_6$-$C_{20}$ aryl, substituted or unsubstituted $C_3$-$C_{40}$ alkyleneoxy; substituted or unsubstituted $C_3$-$C_{40}$ alkylene oxyalkyl; substituted or unsubstituted $C_6$-$C_{40}$ alkylene aryl; substituted or unsubstituted $C_6$-$C_{32}$ aryloxy; substituted or unsubstituted $C_6$-$C_{40}$ alkylene oxyaryl; $C_6$-$C_{40}$ oxyalkylenearyl and mixtures thereof. The use of such substances, in particular in (preferably water-insoluble) microcapsules, corresponds to a preferred embodiment of the invention.

Further particularly preferred fragrance precursors are acetals or ketals, preferably of Formula (IV):

$$R—C(R^1)(OR^3)—OR^2 \quad (IV)$$

where R denotes a linear $C_1$-$C_{20}$ alkyl, branched $C_3$-$C_{20}$ acyl, cyclic $C_6$-$C_{20}$ alkyl, branched cyclic $C_6$-$C_{20}$ alkyl, linear $C_2$-$C_{20}$ alkenyl, branched $C_3$-$C_{20}$ alkenyl, cyclic $C_6$-$C_{20}$ alkenyl, branched cyclic $C_6$-$C_{20}$ alkenyl, substituted or unsubstituted $C_6$-$C_{20}$ aryl, and mixtures thereof; $R^1$ is hydrogen or R; $R^2$ and $R^3$, each independently of one another, are selected from the group composed of linear $C_1$-$C_{20}$ alkyl, branched $C_3$-$C_{20}$ alkyl, cyclic $C_3$-$C_{20}$ alkyl, branched cyclic $C_6$-$C_{20}$ alkyl, linear $C_6$-$C_{20}$ alkenyl, branched $C_6$-$C_{20}$ alkenyl, cyclic $C_6$-$C_{20}$ alkenyl, branched cyclic $C_6$-$C_{20}$ alkenyl, $C_6$-$C_{20}$ aryl, substituted $C_7$-$C_{20}$ aryl, and mixtures thereof. The use of such substances, in particular in (preferably water-insoluble) microcapsules, corresponds to a preferred embodiment of the invention.

Further particularly advantageous fragrance precursors suitable for use conform to Formula (V)

$$R^4O—C(OR^1)(OR^3)—OR^2 \quad (V)$$

where $R^1$, $R^2$, $R^3$ and $R^4$, independently of one another, are linear, branched or substituted $C_1$-$C_{20}$ alkyl; linear, branched or substituted $C_2$-$C_{20}$ alkenyl; substituted or unsubstituted cyclic $C_5$-$C_{20}$ alkyl; substituted or unsubstituted $C_6$-$C_{20}$ aryl, substituted or unsubstituted $C_2$-$C_{40}$ alkyleneoxy; substituted or unsubstituted $C_3$-$C_{40}$ alkylene oxyalkyl; substituted or unsubstituted $C_6$-$C_{40}$ alkylene aryl; substituted or unsubstituted $C_6$-$C_{32}$ aryloxy; substituted or unsubstituted $C_6$-$C_{40}$ alkylene oxyaryl; $C_6$-$C_{40}$ oxyalkylene aryl; and mixtures thereof. The use of such substances, in particular in (preferably water-insoluble) microcapsules, corresponds to a preferred embodiment of the invention.

It is particularly preferable if the fragrances used comprise silicic acid ester mixtures. Silicic acid esters are described, for example, by Formula (V)

$$R—(—O—Si(OR)_2—)_n—OR \quad (V)$$

where each R is independently selected from the group containing H, linear or branched, saturated or unsaturated, substituted or unsubstituted $C_1$-$C_6$ hydrocarbon radicals and fragrance alcohol radicals and/or biocide alcohol radicals, m adopts values from the range of 1 to 20, and n adopts values from the range of 2 to 100. Preferably, the silicic esters of the formulae contain at least one fragrance alcohol radical and/or biocide alcohol radical.

The silicic acid ester mixtures can be used in encapsulated, but also unencapsulated, form. The presence of silicic acid ester mixtures often makes it possible to even further improve the fragrance impression obtainable, with respect to both pleasant aroma and intensity. The fragrance impression is not only better from a qualitative standpoint, i.e. with respect to pleasant aroma, but is also longer-lasting.

The silicic acid ester mixtures can also be contained in the microcapsules. If the silicic acid ester mixtures in the microcapsules preferably account for at least 2 wt % of the total amount of encapsulated fragrances, i.e. in wt % relative to the amount of encapsulated fragrances, this constitutes a preferred embodiment of the invention, which provides a further improvement in the desired fragrance effect after drying.

Particularly suitable fragrance precursors are reaction products of compounds comprising at least one primary and/or secondary amine group, for example an aminofunctional polymer, in particular an aminofunctional silicone, and a fragrance component selected from a ketone, an aldehyde, and mixtures thereof. Suitable flavoring agents are, for example, peppermint oil, spearmint oil, anise oil, star anise oil, cumin oil, eucalyptus oil, fennel oil, lemon oil, wintergreen oil, clove oil, menthol and the like.

Examples of flavorings include: acetophenone, allyl caproate, α-ionone, β-ione, anisaldehyde, anisyl acetate, anisyl formate, benzaldehyde, benzothiazole, benzyl acetate, benzyl alcohol, benzyl benzoate, β-ionone, butyl butyrate, butyl caproate, butylidene phthalide, carvone, camphene, caryophyllene, cineol, cinnamyl acetate, citral, citronellol, citronellal, citronellyl acetate, cyclohexyl acetate, cymene, damascone, decalactone, dihydrocoumarin, dimethyl anthranilate, dimethyl anthranilate, dodecalactone, ethoxyethyl acetate, ethylbutyric acid, ethyl butyrate, ethyl caprinate, ethyl caproate, ethyl crotonate, ethyl furaneol, ethyl guaiacol, ethyl isobutyrate, ethyl isovalerate, ethyl lactate, ethyl methyl butyrate, ethyl propionate, eucalyptol, eugenol, ethyl heptylate, 4-(p-hydroxyphenyl)-2-butanone, γ-decalactone, geraniol, geranyl acetate, geranyl acetate, grapefruit aldehyde, methyl dihydrojasmonate (e.g. Hedion®), heliotropin, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl caproate, trans-2-hexenyl caproate, cis-3-hexenylformate, cis-2-hexyl acetate, cis-3-hexyl acetate, trans-2-hexyl acetate, cis-3-hexylformate, para-hydroxybenzyl acetone, isoamyl alcohol, isoamyl isovalerate, isobutyl butyrate, isobutyraldehyde, isoeugenol methyl ether, isopropyl methylthiazole, lauric acid, levulinic acid, linalool, linalool oxide, linalyl acetate, menthol, menthofuran, methyl anthranilate, methyl butanol, methyl butyric acid, 2-methylbutyl acetate, methyl caproate, methyl cinnamate, 5-methyl furfural, 3,2,2-methyl cyclopentenolone, 6,5,2-methyl heptenone, methyl dihydrojasmonate, methyl jasmonate, methyl 2-methyl butyrate, 2-methyl-2-pentenolic acid, methyl thiobutyrate, 3,1-methyl thiohexanol, 3-methyl thiohexyl acetate, nerol, neryl acetate, trans,trans-2,4-nonadienal, 2,4-nonadienol, 2,6-nonadienol, 2,4-nonadienol, nootkatone, 5-octalactone, gamma octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl alcohol, phenylethyl isovalerate, piperonal, propionaldehyde, propyl butyrate, pulegon, pulegol, sinensal, sulfurol, terpinene, terpineol, terpinolene, 8,3-thiomenthanone, 4,4,2-thiomethyl pentanone, thymol, δ-undecalactone, γ-undecalactone, valencene, valeric acid, vanillin, acetoin, ethylvanillin, ethylvanillin isobutyrate (=3-ethoxy-4-isobutyryl oxybenzaldehyde), 2,5-dimethyl-4-hydroxy-3(2H)-furanone and the derivatives thereof (and preferably homofuraneol (=2-ethyl-4-hydroxy-5-methyl-3(2H)-furanone), homofuronol (=2-ethyl-5-methyl-4-hydroxy-3(2H)-furanone, and 5-ethyl-2-methyl-4-hydroxy-3(2H)-furanone), maltol and maltol derivatives (preferably ethyl maltol), coumarin and coumarin derivatives, γ-lactones (and preferably γ-undecalactone, γ-nonalactone, γ-decalactone), δ-lactones (preferably 4-methyl δ-decalactone, massoia lactone, δ-decalactone, and tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, acetic acid isoamyl ester, butyric acid ethyl ester, butyric acid-n-butyl ester, butyric acid isoamyl ester, 3-methyl-butyric acid ethyl ester, n-hexanoic acid ethyl ester, n-hexanoic acid allyl ester, n-hexanoic acid-n-butyl ester, n-octanoic acid ethyl ester, ethyl-3-methyl-3-phenylglycidate, ethyl-2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio)furan, 2-methyl-3-furanthiol, bis(2-methyl-3-furyl)disulfide, furfuryl mercaptan, methional, 2-acetyl-2-thiazoline, 3-mercapto-2-pentanone, 2,5-dimethyl-3-furanthiol, 2,4,5-trimethyl thiazole, 2-acetylthiazole, 2,4-dimethyl-5-ethylthiazole, 2-acetyl-1-pyrroline, 2-methyl-3-ethyl pyrazine, 2-ethyl-3,5-dimethyl pyrazine, 2-ethyl-3,6-dimethyl pyrazine, 2,3-diethyl-5-methyl pyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyl tridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnamaldehyde, cinnamyl alcohol, methyl salicylate, isopulegol and (not explicitly stated here) stereoisomers, enantiomers, positional isomers, diastereomers, cis/trans-isomers, or epimers of these substances.

Preferably, mixtures of various fragrances (from the various fragrance classes mentioned above) are used which combine to produce an attractive scent note. In this case, the total amount of the at least one fragrance is the amount of all of the fragrances in the mixture together relative to the total amount of the agent.

Dyes

Substances that are suitable and approved for cosmetic purposes can be used as dyes, such as those listed in the publication "Cosmetic Coloring Agents" of the Colorant Commission of the German Research Foundation, Verlag Chemie, Weinheim, 1984, pp. 81-106. Examples include Cochineal Red A (C.I. 16255), Patent Blue V (C.I. 42051), indigotin (C.I. 73015), chlorophyllin (C.I. 75810), Quinoline Yellow (C.I. 47005), titanium dioxide (C.I. 77891), Indanthrene Blue RS (C.I. 69800) and madder lake (C.I.58000). Luminol can also be included as a luminescent dye. These dyes are ordinarily used in concentrations of 0.001 to 0.1 wt %, relative to the total mixture.

The total amount of the auxiliary substances and additives can be 1 to 50, and preferably 5 to 40 wt % relative to the dyes. The production of the dyes can be carried out by common cold or hot processes; the phase inversion temperature method is preferred.

The following known approved food dyes are also suitable:

| Allurarot AC | E 129 | red |
| Aluminum | E 173 | silver-grey |
| Amaranth | E 123 | red |
| Anthocyanins | E 163 | violet, blue |
| Azorubin | E 122 | red |
| Betanin | E 162 | red |
| Brown FK | E 154 | yellowish-brown |
| Brown HT | E 155 | reddish-brown |
| Brilliant Blue FCF | E 133 | blue |
| Brilliant Black BN | E 151 | violet, brown, black |
| Calcium carbonate | E 170 | |
| Canthaxanthin | E 161 g | |
| Carotene | E 160 a | |
| Annatto (Norbixin) | E 160 b | |

-continued

| | | |
|---|---|---|
| Capsanthin | E 160 c | |
| Lycopene | E 160 d | |
| 8'-β-apo-8'-carotenal | E 160 e | |
| Ethyl 8'-apo-β-caroten-8'-oate | E 160 f | |
| Quinoline Yellow | E 104 | |
| Chlorophyll | E 140 | green |
| Cochineal Red A | E 124 | |
| Curcumin | E 100 | |
| Iron oxide | E 172 | |
| Erythrosine | E 127 | |
| Orange Yellow S | E 110 | |
| Gold | E 175 | |
| Green S | E 142 | |
| Indigotin | E 132 | |
| Cochineal | E 120 | |
| Copper-containing complexes of chlorophylls and chlorophyllins | E 141 | |
| Lactoflavin | E 101 | |
| Lithol Rubine BK | E 180 | |
| Lutein | E 161 b | |
| Patent Blue V | E 131 | |
| Vegetable carbon | E 153 | |
| Riboflavin (vitamin B2) | E 101 | |
| Riboflavin 5-phosphate | E 101 a | |
| Safflower | cherry red to brownish-yellow | |
| Silver | E 174 | |
| Tartrazine | E 102 | lemon yellow |
| Titanium dioxide | E 171 | |
| Caramel | E 150 a | |
| Caustic sulfite caramel | E 150 b | |
| Ammonia caramel | E 150 c | |
| Ammonia sulfite caramel | E 150 d | |
| Zeaxanthin | E 161 h | |

Dyes are to be distinguished from coloring food products, which can also be used here. In contrast to the dyes, whose exact composition is prescribed by law and have been evaluated for safety by regulatory agencies with respect to their effects on human health, extracts from foods that have a coloring effect are being increasingly used. Examples include spinach extract (green noodles, pistachio ice cream), red beet extract, and curcumin extract.

INDUSTRIAL APPLICABILITY

The capsules according to the invention can be used in virtually any area, particularly in areas in which active ingredients and active ingredient substances are to be stabilized in order to incorporate them into a composition, so that they can later be released in a controlled manner over a specified period of time.

The capsules according to the invention are particularly suitable for incorporating active ingredients and active substances into cosmetic products or pharmaceutical agents and stabilizing them. In particular, they are used in the production of pharmaceutical agents or cosmetic products for use on the skin or oral use.

The capsules according to the invention are advantageous in that they can have a high content and may enclose any type of active ingredients and active substances. In particular, the capsules according to the invention are usable in the area of food products, because they are toxicologically safe.

EXAMPLES

Example 1

Production of Alginate Based Capsules

Alginate and gum arabic are fully dissolved in an amount of water heated to 40° C. while stirring. Wheat fibers are added to this mixture in homogeneous distribution. If coloring is desired, the dye is first dissolved in the flavoring agent. The flavoring agent is then added to the previously produced mixture and homogeneously dispersed (Ultra TurraxP or homogenizer). The mixture is added dropwise to a calcium hardening bath adjusted to a temperature of 7-10° C. The resulting capsules are sieved off, washed, and dried in the fluidized bed.

Both alginate and pectin based capsules were produced as described above in which an active ingredient (e.g. a flavoring agent) was encapsulated.

In one case, an amidated pectin was used that could be applied exactly like the alginate in comparable formulations.

Moreover, mixtures of low-esterified pectins (e.g. citrus pectin, apple pectin, other low-esterified pectins) with alginates were tested, with a ratio of alginate to pectin in the range of 1:2 to 2:1.

Moreover, alginate-gellan based capsules were produced as specified above, with the range of ratio of alginate to gellan being in the range of 3:2 to 3:1.

TABLE 1

Alginate-gellan gum based capsules

| Components | K1 wt % | K2 wt % | K3 wt % | K4 wt % |
|---|---|---|---|---|
| Alginate | 1.03 | 1.18 | — | 0.68 |
| Pectin | — | — | 1.33 | 0.65 |
| Gum arabic | 0.65 | 0.74 | 0.83 | 0.83 |
| Wheat fibers | 0.56 | 0.64 | 0.77 | 0.77 |
| Flavoring agent | 6.89 | 7.88 | 8.82 | 8.82 |
| Colorant | 0.02 | 0.02 | 0.02 | 0.02 |
| Gellan gam | 0.37 | 0.84 | — | — |
| Water | Add to 100 | Add to 100 | Add to 100 | Add to 100 |
| Content | Approx. 75% | Approx. 75% | Approx. 75% | Approx. 75% |

The resulting alginate-gellan gum capsules show an average size of 925 to 955, with use of a 0.5 mm nozzle, temp. dispersion of 40° C., temp. cal. bath 10-15° C., pressure dispersion of 0.19 bar, frequency of 250 Hz, amplitude of 0.75 A, temp. hardening bath 7-10° C., flow rate 0.8 kg/h, drying with silicon diox. 103846 approx. 10%, and Aeromatic drying at 45° C. for approx. 35 min to 45 min.

The ratios of the components in the standard formulation of a gel bead before and after drying are as follows for alginate capsules:

TABLE 3

Ratio of individual components in an alginate capsule

| Components | Before drying wt % | After drying wt % |
|---|---|---|
| Water | 88.231 | — |
| Flavoring agent | 8.823 | 75.11 |
| Sodium alginate E401 high viscous | 1.325 | 11.28 |
| Gum arabic type SEYAL | 0.827 | 7.00 |
| Wheat fibers WF 600-30 | 0.772 | 6.57 |

Example 2

Production of an O/W Emulsion

Mixtures A and B were separately heated to 80° C., and mixture B was then dispersed in mixture A. Mixture C was then added to mixture AB and emulsified using an Ultra Turrax Stirrer (3 min). After this, the emulsion was neutralized with D and cooled. The capsules according to the invention (E) were incorporated into emulsions E1 and E2 and could thus be tested.

TABLE 2

O/W emulsions into which the capsules according to the invention are incorporated

|   | Raw material | INCI | E1 w/w % | E2 w/w % |
|---|---|---|---|---|
| A. | Emulsiphos | Potassium Cetyl Phosphate, Hydrogenated Palm Glycerides | 2.0 | 2.0 |
|   | Cutina PES | Pentaerythrityl Distearate | 2.0 | 2.0 |
|   | PCL Solid | Stearyl Heptanoate, Stearyl Caprylate | 2.0 | 2.0 |
|   | Lanette O | Cetearyl Alcohol | 2.5 | 2.5 |
|   | PCL Liquid 100 | Cetearyl Ethylhexanoate | 5.0 | 5.0 |
|   | Isodragol | Triisononanoin | 2.0 | 2.0 |
|   | Dow Corning 246 Fluid | Cyclohexasiloxane, Cyclopentasiloxane | 2.0 | 2.0 |
|   | Dragoxat 89 | Ethylhexyl Isononanoate | 3.0 | 3.0 |
| B. | Ultrez-10 | Carbomer | 0.2 | 0.2 |
|   | Keltrol CG | Xanthan Gum | 0.15 | 0.15 |
| C. | Wasser | Water (Aqua) | 71.05 | 71.15 |
|   | EDTA BD | Disodium EDTA | 0.1 | — |
|   | Hydrolite-5 | Pentylene Glycol | 2.0 | 2.0 |
|   | Propylene Glycol | Propylene Glycol | 2.0 | 2.0 |
|   | SymDiol 68 | 1,2 Hexanediol, Caprylyl Glycol | 0.6 | 0.6 |
|   | Glycerin 85% | Glycerin | 2.0 | 2.0 |
| D. | Sodium Hydroxide 10% sol. | Sodium Hydroxide | 0.4 | 0.4 |
| E. | Capsules K2 according to the invention | (75% active) | 1.0 | 1.0 |

Example 3

Storage Tests

The emulsions of example 2, which the capsules according to the invention contain, were stored at various temperatures and visually and microscopically examined.

TABLE 3

Storage test results

| | T = 5° C. | T = RT | | T = 40° C. | | |
|---|---|---|---|---|---|---|
| Emulsion | 3 months | 2 days | 3 months | 1 week | 2 weeks | 3 months |
| E1 | — | All capsules decomposed | — | — | — | — |
| E2 | Stable | Stable | Stable | Stable | Stable | Capsules slightly swollen, but still recognizable as particles |

Emulsion 1 with EDTA no longer showed any capsules after 2 days at RT. After 2 days, all capsules were destroyed and dissolved in the emulsion. Emulsion 2 showed better stability at various storage temperatures. Even after 3 months, capsules were still visible and microscopically detectable in the emulsion, although the capsules were slightly swollen after 3 months of storage. When the emulsion was rubbed onto the skin, the capsules disintegrated and released the active ingredient.

Example 4

Storage Tests in Products

The dried capsules according to the invention were incorporated into toothpaste, margarine and skin cream and stored after 3 months at room temperature.

The dried capsules were stable after 3 months and showed no changes whatsoever. As for the capsules that had been incorporated into toothpaste, the alginate or pectin based capsules were highly swollen, but the capsule structure remained recognizable. The capsules based on alginate-gellan gum showed improved stability. These capsules were still stable after 1 month of storage at RT.

In the margarine and the skin cream, the capsules remained stable even after 3 months.

Example 5

Formulation Examples A to G

Chewing Gum Pastes A-C

The capsules according to the invention were incorporated into chewing gum pastes as shown in Table 4.

TABLE 4

Chewing gum pastes A-C

| Composition | A | B | C |
|---|---|---|---|
| Polyisobutylene (MW 20,000) | 20.0 | 25.0 | 30.0 |
| Sorbitol | 51.0 | 47.5 | 44.5 |
| Mannitol | 5.0 | 4.3 | 3.6 |
| Glycerol | 8.0 | 8.0 | 7.0 |
| Lycasin:glycerol (1:1) | 8.2 | 8.0 | 7.0 |
| Lecithin | 0.2 | 0.2 | 0.2 |
| Flavoring mixture | 1.0 | 1.0 | 1.0 |
| Water | | to 100 | |

Cosmetic Compositions D-G Containing Capsules According to the Invention

In D and E, flavoring agents were incorporated into the capsules according to the invention.

In creams F and G, cooling agents were incorporated into the capsules according to the invention.

D=bath lotion, E=soft cream, F, G=moisturizing cream

TABLE 5

Example formulations D-G of a cosmetic preparation

| Components (INCI) | D | E | F | G |
|---|---|---|---|---|
| Texapon ® NSO<br>Sodium Laureth Sulfate | — | — | — | — |
| Plantacare ® 818<br>Coco Glucosides | — | — | — | — |
| Plantacare ® PS 10<br>Sodium Laureth Sulfate (and) Coco Glucosides | 22.0 | — | — | — |
| Dehyton ® PK 45<br>Cocamidopropyl Betaine | 15.0 | — | — | — |
| Emulgade ® SE<br>Glyceryl Sterate (and) Ceteareth 12/20 (and) Cetearyl Alcohol (and) Cetyl Palmitate | — | 5.0 | 5.0 | 4.0 |
| Eumulgin ® B1<br>Ceteareth-12 | — | — | — | 1.0 |
| Lameform ® TGI<br>Polyglyceryl-3 Isostearate | — | — | — | — |
| Dehymuls ® PGPH<br>Polyglyceryl-2 Dipolyhydroxystearate | — | — | — | — |
| Monomuls ® 90-O 18<br>Glyceryl Oleate | — | — | — | — |
| Cetiol ® HE<br>PEG-7 Glyceryl Cocoate | 2.0 | — | — | — |
| Cetiol ® OE<br>Dicaprylyl Ether | — | — | — | — |
| Cetiol ® PGL<br>Hexyldecanol (and) Hexyldecyl Laurate | — | — | — | 3.0 |
| Cetiol ® SN<br>Cetearyl Isononanoate | 1.0 | 3.0 | 3.0 | — |
| Cetiol ® V<br>Decyl Oleate | — | 3.0 | 3.0 | — |
| Myritol ® 318<br>Coco Caprylate Caprate | — | — | — | 3.0 |
| Bees Wax | — | — | — | — |
| Nutrilan ® Elastin E20<br>Hydrolyzed Elastin | — | 2.0 | — | — |
| Nutrilan ® I-50<br>Hydrolyzed Collagen | — | — | 2.0 | — |
| Gluadin ® AGP<br>Hydrolyzed Wheat Gluten | 0.5 | — | — | 0.5 |
| Gluadin ® WK<br>Sodium Cocoyl Hydrolyzed Wheat Protein | 2.0 | — | — | — |
| Euperlan ® PK 3000 AM<br>Glycol Distearate (and) Laureth-4 (and) Cocamidopropyl Betaine | 5.0 | — | — | — |
| Arylpon ® F<br>Laureth-2 | — | — | — | — |
| Hydagen ® CMF<br>Chitosan | 1.0 | 1.0 | 1.0 | 1.0 |
| Capsules according to the invention | 1.0 | 1.0 | 1.0 | 1.0 |
| Glycerol (86 wt. %) | — | 3.0 | 3.0 | 5.0 |
| Water add to | 100 | 100 | 100 | 100 |

The invention claimed is:

1. A method for the production of a water-insoluble capsule, comprising:
   (i) forming an emulsion of a) at least one gelable substance, b) at least one emulsifier, c) at least one filler, and d) at least one active ingredient,
   (ii) dropwise adding the emulsion of (i), containing the active ingredient, to a solution comprising a multivalent cation, wherein crosslinking occurs, gelation takes place, and the water-insoluble capsules are formed to include the active ingredient,
   (iii) separating the capsule, containing the active ingredient, formed from step (ii); and
   (iv) drying the capsule obtained from step (iii) to obtain a water-insoluble capsule.

2. The method of claim 1, wherein the gelable substance is selected from the group consisting of alginate, pectin, gellan gum and mixtures thereof.

3. The method of claim 1, wherein the emulsifier is selected from the group consisting of polysorbates, sugar esters, saponins, gum arabic, modified gum arabic, modified starch and mixtures thereof.

4. The method of claim 1, wherein the filler is selected from the group consisting of vegetable fibers, microcrystalline cellulose, silica gels, native starch, silicates and mixtures thereof.

5. The method of claim 1, wherein the at least one active ingredient is selected from the group consisting of flavorings, fragrances, dietary supplements, cosmetic active substances, pharmaceutically active substances, and mixtures thereof, said active ingredient being different from the filler.

6. The method of claim 5, wherein the capsules comprise a water-insoluble matrix of the multivalent cation and the filler, with the active ingredient encapsulated in the matrix and the active ingredient comprises between 20 and 95 wt % of the capsule.

7. The method of claim 5, wherein the filler is a vegetable fiber selected from the group consisting of apple fibers, bamboo fibers, oat fibers, pea fibers, potato fibers, wheat fibers and mixtures thereof.

8. The method of claim 5, wherein the emulsifier is selected from the group consisting of gum arabic, modified gum arabic, modified starch and mixtures thereof.

9. The method of claim 5, wherein the ratio of the emulsifier to the filler is in the range of 2:1 to 1:2.

10. The method of claim 5, wherein the active ingredient content of the capsules is between 20 and 60 wt %.

11. The method of claim 5, wherein the capsules have a mean average diameter of 200 to 1500 μm.

12. The method of claim 5, wherein the cation is a calcium ion.

13. A method for preparing a cosmetic product, pharmaceutical composition, food or beverage comprising preparing the capsule as claimed in claim 1 and adding the capsule to the cosmetic product, pharmaceutical composition, food or beverage.

14. A method for preparing a pharmaceutical composition or cosmetic product for use on skin or orally, comprising preparing the capsule as claimed in claim 1 and adding the capsule to the pharmaceutical composition or cosmetic product for use on the skin or for oral use.

15. A method for the controlled, prolonged, delayed delivery and release of an active ingredient, comprising preparing the capsule as claimed in claim 1 and adding the capsule to a cosmetic product, pharmaceutical composition, food or beverage, and administering the cosmetic product, pharmaceutical composition, food or beverage to a user.

16. A method for preparing a water-insoluble capsule, comprising:
   (i) forming an emulsion of at least one gelable substance, at least one emulsifier, at least one filler, and at least one active ingredient,
   (ii) adding drops of the emulsion to an alcohol-based solution containing a multivalent cation, and initiating crosslinking and gelation of the gelable substance, the at least one emulsifier, the at least one filler, and the at least one active ingredient or active substance to form capsules, (iii) separating the capsules formed in step (ii), and
(iv) drying the capsules, wherein
the gelable substance is selected from the group consisting of alginate, pectin, agar-agar, carrageenan, gellan gum, gelatins, modified cellulose, proteins and mixtures thereof,
the emulsifier is selected from the group consisting of polysorbates, sugar esters, saponins, gum arabic, modified starch and mixtures thereof, and
the filler is selected from the group consisting of vegetable fibers, microcrystalline cellulose, silica gels, native starches, silicates and mixtures thereof.

17. The method of claim 16, wherein the alcohol-based solution contains calcium ions and the filler comprises a vegetable fiber selected from the group consisting of apple fibers, bamboo fibers, oat fibers, pea fibers, potato fibers, wheat fibers and mixtures thereof.

* * * * *